(12) United States Patent
Broyles et al.

(10) Patent No.: US 7,517,669 B2
(45) Date of Patent: Apr. 14, 2009

(54) GENE REGULATION THERAPY INVOLVING FERRITIN

(76) Inventors: Robert H. Broyles, 212 NW. 20th St., Oklahoma City, OK (US) 73103; Robert A. Floyd, 6201 Harden Dr., Oklahoma City, OK (US) 73118

(*) Notice: Subject to any disclaimer, the term of this patent is extended or adjusted under 35 U.S.C. 154(b) by 0 days.

(21) Appl. No.: 10/003,669

(22) Filed: Nov. 1, 2001

(65) Prior Publication Data
US 2002/0128183 A1 Sep. 12, 2002

Related U.S. Application Data

(60) Provisional application No. 60/245,003, filed on Nov. 1, 2000.

(51) Int. Cl.
*C12P 21/06* (2006.01)
(52) U.S. Cl. .............. 435/69.1; 435/455; 424/93.2; 424/93.21
(58) Field of Classification Search ............ 514/2; 530/350; 424/450, 178.1
See application file for complete search history.

(56) References Cited

U.S. PATENT DOCUMENTS 4,582,820 A * 4/1986 Teng .............. 514/3

OTHER PUBLICATIONS

Mankad, Pediatric Pathlol Mol Med 2001;20:1-13.*
Bowie et al, Science Mar. 1990; 247:1306-10.*
Rudinger, Peptide Hormones 1976; June;pp. 1-7.*
Buckel, Trends Pharmacol Sci 1996;17:450-6.*
Welch et al, Free Radic Biol Med 2002;33:399-408.*
Schwarze et al, Trends Cell Biol Jul. 2000; 10:290.*
Herzog et al, Expert Rev Cardiovascular Ther 2003;1:215-32.*
Myron-Holtz et al, Blood 1999;94:3205-11.*
Leimberg et al, Am J Hematol 2003;73:211-2.*
Puthenveetil et al, Curr Hematology Reports 2004;3:298-305.*
Thompson et al, J Cell Sci 2002;115:2165-77.*
Insulin and Diabetes, Pubmed 2005.*
Files et al, J Pediatric Hematol Oncol 2002:24:284-90.*
Broxmeyer et al, PNAS 1991;88:770-4.*
Lloyd et al. Mole Cell Biol 1992;12:1561-7.*
Abruzzese et al., *Molecular Therapy*, 2(3):276-287, 2000.
Ammendola et al., *J. Biol. Chem.*, 267(25):17944-17948, 1992.
Andrews et al., *Nature*, 362:722-8, 1993.
Applegate et al., *J. Invest. Dermatol.*, 111(1):159-163, 1998.
Armstrong et al., *Cell*, 95:93-104, 1998.
Arosio et al., *Cancer Res.*, 36:1735-1739, 1976.
Atkinson et al., *Biochem Cell Biol*, 67:52-7, 1989.
Aziz et al., *Proc Natl Acad Sci USA*, 84:8478-82, 1987.
Barker-Harrel et al., *Exp. Cell Res.*, 178:435-448, 1988.
Bartzokis et al., *Arch Neurol.*, 56:569-574, 1999.
Berg et al., *Nucleic Acids Res*, 17:8833-52, 1989.
Bettan et al., *Molecular Therapy*, 2(3):204-210, 2000.
Bieker, J.J., *Curr Opin Hematol*, 5(2):145-50, 1998, Abstract.

Bieker et al., *Ann NY Acad. Sci*, 850:64-69, 1998.
Blau et al., *Curr Opin Hematol*, 1(2):136-42, 1994, Abstract.
Bodine, D., *Molecular Therapy*, 2(2):101-102, 2000.
Bristol et al., *Molecular Therapy*, 2(3):223-232, 2000.
Broyles, R.H. *Sem. Cell Develo. Biol.*, 10:259-265, 1999.
Broyles et al., Colloque *INSERM*, 234:43-51, 1995.
Broyles et al., *PNAS*, 98(16):9145-9150, 2001.
Cai et al., *J. Biol. Chem.*, 272(19):12831-12839, 1997.
Cai et al., *Mol. Biol. Cell*, 9:1037-51, 1998.
Casey et al., *Science*, 240:924-928.
Chang et al., *DNA Cell Biol.*, 9(3):205-212, 1990.
Cheepsunthorn et al., *J. Comp. Neurol.*, 400:73-86, 1998.
Chen et al., *Molecular Therapy*, 2(3):256-261, 2000.
Dean et al., *Prog. Clin. Biol. Res.*, 134:323-24, 1983.
Dean et al., *Proc. Natl Acad Sci USA*, 80:5515-9, 1983.
deBoer et al. *Embo J*, 7(13):4203-4212, 1988.
Dickey et al., *J. Biol. Chem.*, 262(16):7901-7907, 1987.
Dignam et al., *Nucleic Acid Res*, 11(5):1475-89, 1983.
Donze et al., *J. Biol. chem*, 270(4):1955-9, 1995.
Dover et al., *Blood*, 69(4):1109-13, 1987.
Epner et al., *Mol. Cell*, 2:447-55, 1998.
Ferreira et al., *J. Biol. Chem.*, 275(5):3021-3024, 2000.
Fordis et al., *Prog. Clin. Biol. Res.*, 191:281-92, 1985.
Fordis et al., *Biochem Biophys Res. Commun.*134(1):128-33, 1986.
Fried et al., *Nucleic Acids Res*, 9(23):6505-25, 1981.
Gao et al., *Molecular Therapy*, 2(2):233-244, 2000.
Gribnau et al., *Mol. Cell*, 5:377-86, 2000.
Griffiths et al., *Brain*, 122:667-673, 1999.
Gumucio et al., *Proc Natl Acad Sci USA*, 90:6018-22, 1993.
Haile et al., *Proc Natl Acad Sci USA*, 89:11735-9, 1992.
Harrison et al., *Biochim Biophys Acta*, 1275:161-203, 1996.
Hengge et al., *Molecular Therapy*, 2(3):188-194, 2000.
Hentze et al., *Proc Natl Acad Sci USA*, 83:7226-30, 1986.
Hentze et al., *Science*, 238:1570-3, 1987.

(Continued)

*Primary Examiner*—Q. Janice Li
(74) *Attorney, Agent, or Firm*—Dunlap Codding, P.C.

(57) ABSTRACT

A method is described for regulating gene expression related to iron metabolism to ameliorate diseases that include sickle cell disease, cancers, neurodegenerative diseases, Friedreich's ataxia and other neuromuscular disorders, and atherosclerosis. This approach is illustrated by recent findings that show that ferritin-H, an iron-binding protein that is present in cell nuclei, can repress the human β-globin gene, the gene that is mutated in sickle cell disease. Increased expression of ferritin-H or a related ferritin-family peptide, given to effected cells either as the peptide itself (or a part thereof), as an expression clone of the ferritin-H-subfamily gene, or via a gene regulator that increases expression of the ferritin-H-subfamily gene itself, prevents or ameliorates expression of the disease state in disorders where increased availability of iron is implicated in the etiology of the disease, including those named above.

5 Claims, 13 Drawing Sheets

OTHER PUBLICATIONS

Higgs, D.R., *Cell*, 95;299-302, 1998.
Jane et al., *Mol Cell Biol*, 13(6):3272-81, 1993.
Kennedy et al., *Proc Natl Acad Sci USA*, 89:11730-4, 1992.
Kirkali et al., *Urol Int*, 62;21-25, 1999.
Kurien et al., *Anal Biochem*, 245:123-126, 1997.
Li et al., *Proc Natl Acad Sci USA*, 94:2444-8, 1997.
Lin et al., *Arch Biochem Biophys*, 352(1):51-58, 1998.
Lohr et al., *Molecular Therapy*, 2(3):195-203, 2000.
Macleod et al., *Mol Cell Biol*, 11(9):4324-32, 1991.
Maniatis et al., *Molecular Cloning: A Laboratory Manual*, Cold Spring Harbor Laboratory, Cold Spring Harbor, New York, 1982.
Mandishona et al., *Hepatology*, 27(6):1563-1566, 1998.
Matsumoto et al., *Methods in Enzy.*, Academic Press, New York, 316(330:492-511, 2000.
Miller et al., *Mol Cell Biol*, 13(5);2776-86, 1993.
Orkin, S.H., *Eur J Biochem*, 231:271-81, 1995.
Papyannopoulou, *Cell*, 46:469-76, 1986.
Picard et al., *Blood*, 87(5):2057-64, 1996.
Pountney et al., *J Cell Sci*, 112:825-31, 1999.
Reik et al., *Mol Cell Biol.* 18(10): 5992-6000, 1998.
Rodgers et al., *Prog Clin Biol Res*, 316B:281-93, 1989.
Rodgers et al., *Hematologic responses of patients with sickle cell disease to treatment with hydroxyurea*, vol. 322:1037-1045, Apr. 12, 1990.
Sheridan et al., *Molecular Therapy*, 2(3):262-275, 2000.
Shterman et al., *Cancer Res*, 49:5033-6, 1989.
Somiari et al., *Molecular Therapy*, 2(3):178-187, 2000.
Theil, E.C., *Ann Rev Biochem*, 56:289-315, 1987.
Thomson, AJ, *febs Lett*, 285(2):230-6, 1991.
Tsai et al., *Nature*, 339:446-51, 1989.
Wu et al., *J Biol Chem*, 266(26):17566-72, 1991.
Wu et al., *Molecular Therapy*, 2(3):288-298, 2000.
Chase; Binding of HMG-I (Y) Elicits Structural Changes in a Silencer of the Human B-Globin Gene; Jan. 1999; XP008009648.
Broyles et al., "A ferritin-like protein binds a highly conserved CAGTGC motif in the human adult beta clobin gene promoter and can mediate DNA looping in vitro," *FASEB Journal*, Annual Meeting of the American Society for Biochemistry and Molecular Biology, San Fransicso, Califonia, May 21-25, 9(6):A1328, 1995.

* cited by examiner

WT and Mutant Oligonucleotides of -164/-128, 5' β-Globin

| | |
|---|---|
| WT sequence: | 5' AACTCCTAAGCCAGTGCCAGAAGAGCCAAGGACAGGT 3' |
| Mutant #1 (-162/-157): | 5' AAGGGGGGAGCCAGTGCCAGAAGAGCCAAGGACAGGT 3' |
| Mutant #2 (-144/-139): | 5' AACTCCTAAGCCAGTGCCAGAAAAAACAAGGACAGGT 3' |
| Mutant #3 (-135/-130): | 5' AACTCCTAAGCCAGTGCCAGAAGAGCCAACCCCCCGT 3' |
| Mutant #4 (-153/-148): | 5' AACTCCTAAGCAAAAAACAGAAGAGCCAAGGACAGGT 3' |

| Competitor Oligonucleotide | Molar Excess producing 50 % Inhibition |
|---|---|
| Wild type (WT) | 42x |
| Mutant #1 | 30x |
| Mutant #2 | 38x |
| Mutant #3 | 35x |
| Mutant #4 | 850x |

FIG. 5

|  | -162 | -153 | -148 | -142 |
|---|---|---|---|---|
| Human | TCCTAAGC | CAGTGC | CAGAAG | |
| Gorilla | TCCTAAGC | CAGTGC | CAGGAG | |
| Macaca | TCCTAAGC | CAGTGC | CAGAAG | |
| Bovine | TCTAAAGT | CAGTGC | CAGGAA | |
| Goat | TCTAAAGT | CAGTGC | CAGGAA | |
| Sheep | TCTAAAGT | CAGTGC | CAGGAA | |
| Galago | TCCTAAGT | GAGTGC | CAGAAC | |
| Tarsus | CTCTAAGC | CAGTAC | CAGAAC | |
| Lepus | TCCTAAGC | CATTGC | CAGAAC | |
| Rabbit | TCCTAAGC | CATTGC | CATAAC | |
| Rat | CCTGAGGC | CAGTGG | CCCAGC | |
| Mouse | TCTTAAGC | CTGTGC | CATAGC | |

GENE REGULATION THERAPY INVOLVING FERRITIN

CROSS REFERENCE TO PRIOR APPLICATIONS

This application is a continuation-in-part of U.S. provisional patent application No. 60/245,003, filed Nov. 1, 2000, which is hereby incorporated by reference.

BACKGROUND

1. Field of the Invention

The present invention relates to gene regulation therapy involving ferritin. More specifically, the invention relates to the use of Ferritin-H and derivative proteins thereof for regulation of genes related to iron metabolism and regulation.

2. Prior Art

Background for Sickle Cell Disease

Hematopoiesis, or the formation of blood cells, begins in the developing human embryo as clusters of stem cells called blood islands. These cells appear in the yolk sac at about the third week of development and, at about the third month, migrate to the developing liver which becomes the principal site of blood cell formation. Although the spleen, lymph nodes and bone marrow all make small contributions to blood cell development, not until the fourth month does the bone marrow become the principal site of hematopoiesis. At birth, virtually all blood cells originate from the bone marrow. Although small foci of blood-forming cells sometimes persist in the liver for longer periods of time, hepatic blood cell formation has decreased to a trickle. At this time, all of the marrow is actively forming blood cells and continues to do so until after puberty when, at about 18 years of age, the principal sites of blood cell formation become the marrow of the vertebrae, ribs, sternum, skull, pelvis and the proximal epiphyseal regions of the femur and humerus. These areas represent only about half of the available marrow. The cavities which remain are filled with yellow-fatty tissues.

In the adult, hematopoiesis involves the bone marrow, the lymph nodes and the spleen. These organs and associated tissues are traditionally divided into myeloid and lymphoid tissue-types. Myeloid tissues and the cells derived from the myeloid tissue include the erythrocytes, platelets, granulocytes and monocytes. Lymphoid and lymphoid-derived tissues include the thymus, lymph nodes and spleen. The myeloid/lymphoid division is somewhat artificial as these two types of tissues are believed to originate from a single pluripotent stem cell.

Lymphoid and myeloid stem cells, formed from division of the pluripotent cell, are precursors for all subsequent cell types. The committed cell-types for the lymphoid stem cell include the pro-T cells which form mature T cells and the pro-B cells which differentiate into plasma cells. Intermediate cell types can be distinguished based on cell-surface phenomenon such as the expression of immunoglobulin heavy and light chain, Ia protein and other cell surface markers. The three committed cell-types for the myeloid stem cell include E/mega cells which differentiate into the erythrocyte-burst forming unit (BFU-E) followed by the erythrocyte-colony forming unit cells (CFU-E) and megakaryocyte-CFU cells (CFU-mega), granulocyte/macrophage-CFU cells (CFU-G/M) which differentiate into CFU-G and CFU-M cells, and the eosinophil-CFU cells (CFU-Eo) which ultimately form mature eosinophils. Although these committed cell types reside mainly in the marrow, some circulate throughout the body in the blood stream.

The relative proportions of cell types in the bone marrow have a myeloid/erythroid ratio of about three to one comprising about 60% granulocytes and their precursors, about 10% lymphocytes and their precursors, about 20% erythrocytes and their precursors, and about 10% unidentified cells. The predominant myeloid cell types in the marrow cavity are the myelocytes, metamyelocytes and granulocytes. The predominant cell types in the erythroid compartment are the polychromatophilic and orhtochromic normoblasts. Under conditions of normal iron metabolism, about 30% to 40% of the normoblasts contain scattered ferritin granules. These cells are referred to as sideroblasts and the iron granules they contain are reservoirs drawn from as the cells insert iron into protoporphyrin to form heme. The production of heme and the production of globin are precisely balanced within the cell. If either is hindered or depressed, for whatever reason, excess ferritin accumulates in the sideroblasts. This increased iron accumulation can be visualized in the mitochondria, the loci of heme synthesis.

The major function of red blood cells is to transport oxygen to tissues of the body. Minor functions include the transportation of nutrients, intercellular messages and cytokines, and the absorption of cellular metabolites. Anemia, or a loss of red blood cells or red blood cell capacity, can be grossly defined as a reduction in the ability of blood to transport oxygen and may be acute or chronic. Chronic blood loss may be caused by extrinsic red blood cell abnormalities, intrinsic abnormalities or impaired production of red blood cells. Extrinsic or extra-corpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hypersplenism can provoke red blood cell disorders.

Hemoglobin comprises four protein chains, two alpha chains and two beta chains ($\alpha_2 \beta_2$), interwoven together, each with its own molecule of iron and with a combined molecular weight of about 68 kD. The hemoglobin macromolecule is normally glycosylated and upon absorbing oxygen from the lungs transforms into oxyhemoglobin ($HbO_2$). There are at least six distinct forms of hemoglobin, each expressed at various times during development. Hemoglobin in the embryo is found in at least three forms, Hb-Gower 1 ($\xi_2 \epsilon_2$), Hb-Gower 2 ($\alpha_2 \epsilon_2$) and Hb-Portand ($\xi_2 \gamma_2$). Hemoglobin in the fetus comprises nearly totally HbF ($\alpha_2 \gamma_2$), whereas hemoglobin in the adult contains about 96% HbA ($\alpha_2 \beta_2$), about 3% HbA$_2$ ($\alpha_2 \delta_2$) and about 1% fetal HbF ($\alpha_2 \gamma_2$). The embryonic switch of globin expression from $\xi$- to $\alpha$- and from $\epsilon$- to $\gamma$- begins in the yolk sac. However, chains of embryonic $\xi$- and $\epsilon$- have been found in the fetal liver and complete transition to the fetal form does not occur until late in fetal development. The fetal switch from $\gamma$- to $\beta$- begins later in erythropoiesis with the amount of $\beta$-globin produced increasing throughout gestation. At birth, $\beta$-globin accounts for about 40% of non-$\alpha$-globin chain synthesis and thereafter continues to rapidly increase.

Defects or mutations in globin chain expression are common. Some of these genetic mutations pose no adverse or only minor consequences to the person, however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions. For example, substitutions of valine for glutamic acid at the sixth position of the β chain produces HbS and was found to occur in about 30% of black Americans. In the HbS heterozygote, only about 40% of total hemoglobin is HbS with the remainder being the more normal HbA.

Upon deoxygenation, HbS molecules undergo aggregation and polymerization ultimately leading to a morphological distortion of the red cells which acquire a sickle or holly-leaf shape. Sickling has two major consequences, a chronic hemolytic anemia and an occlusion of small blood vessels that results in ischemic damage to tissues. Further, when exposed to low oxygen tensions, polymerization converts HbS hemoglobin from a free-flowing liquid to a viscous gel. Consequently, the degree of pathology associated with sickle cell anemia can be correlated with the relative amount of HbS in the patient's system.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of γ-globin is also observed with other β-globin disorders, such as HbC and HbD, and other mutations of the β chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

To some extent, sickling is a reversible phenomenon. With increased oxygen tensions, sickled cells depolymerize. This process of polymerization-depolymerization is very damaging to red cell membranes and eventually leads to irreversibly sickled cells (ISC) which retain their abnormal shape even when fully oxygenated. The average ISC survives for about 20 days in the body, as compared to the normal 120 day life span. Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities or joints. Leg ulcers are an additional manifestation of the vaso-occlusive tendency of this disease. Central nervous system involvement is common producing seizures and even strokes. Aplastic crises, also common, represent a temporary cessation of bone marrow activity and may be triggered by infections, folic acid deficiency or both. Crises are episodic and reversible, but may be fatal. Damage from crisis episodes tends to be cumulative and even in those individuals with milder forms of sickle cell disorders, life-spans can be greatly reduced. Absent alternative intervention, patients typically die before the age of 30.

Anti-gelling compounds including clofibric acid ($ClC_6H_5OC(CH_3)_2COOH$), p-chlorophenoxy acetic acid ($ClC_6H_5OCH_2COOH$), and phenoxy acetic acid ($C_6H_5OCH_2COOH$) have been shown to prophylactically inhibit polymerization in artificially deoxygenated blood. It was speculated that these compounds may be useful in a narrow respect to prevent blood cell sickling in sickle cell disease. Such treatments may potentially decrease the frequency of symptomatic episodes caused by vaso-occlusive crises if enough of the chemical can be administered to bind all hemoglobin in the body.

The thalassemia syndromes are a heterogenous group of disorders all characterized by a lack of or a decreased synthesis of the globin chains of HbA. Deficiencies of β-globin expression are referred to as β-thalassemias and deficiencies of α-globin, α-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of α- or β-globin protein.

Mammalian globin gene expression is highly regulated during development. The basic structure of the α- and β-globin genes are similar as are the basic steps in synthesis of α- and β-globin. There are at least five human α-globin genes located on chromosome 16 including two adult α-globin genes of 141 amino acids that encode identical polypeptides and differ only in their 3'-untranslated regions, one embryonic a gene Z(ζ), and at least two pseudo-α genes, psi zeta (ΨZ) and omega alpha (ωα).

The human β-globin gene cluster includes one embryonic gene, epsilon (ε), two adult beta globin genes, beta (β) and delta (δ), two fetal beta globin genes G-gamma (G-γ) and A-gamma (A-γ.), which differ by only one amino acid, and at least one pseudo-beta gene, psi beta (Ψβ). All are expressed from a single 43 kilobase segment of human chromosome 11. Fetal β-type globin, or γ-globin, is expressed in the earliest stages of mammalian development and persists until about 32 to 34 weeks of gestation. At this stage, the adult forms of β-globin begin to be expressed and substitute for the fetal proteins. Studies correlating clinical hematological results with the locations of various mutations that correspond to switching indicate that a region located upstream of the 5'-end of the δ-gene may be involved in the cis suppression of γ-gene expression in adults. The stimulus for this switch from fetal to adult protein is unknown.

Each β-globin gene comprises three exons which encode about 146 amino acids, two introns and a 5'-untranslated region containing the promoter sequences and a 3' untranslated region. Biosynthesis of β-globin begins with transcription of the entire gene followed with RNA processing of the message, removal of the introns by splicing, poly A addition, capping and post-transcriptional modifications. The mature mRNA molecule is exported from the nucleus and translated into β-globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations. β°-thalassemias are characterized by a complete absence of any β-globin chains; β⁺-thalassemias are characterized by a detectable presence of a reduced amount of β chains.

There are three principal categories of β-thalassemia, thalassemia major, thalassemia intermedia and thalassemia minor. Patients with thalassemia minor may be totally asymptomatic and are genotypically β⁺/β or β°/β. Although red cell abnormalities can be detected, symptoms are mild. Thalassemia intermedia patients are most often genotypically β⁺/β⁺ or β°/β and present severe symptoms which can be alleviated with infrequent blood transfusions. In contrast, thalassemia major patients are genotypically β°/β°, β°/β⁺ or β⁺/β⁺, and require regular and frequent transfusions. Children suffer from severe growth retardation and die at an early age from the profound effects of anemia. Those that survive longer suffer from morphological changes. The face becomes distorted due to expansion of marrow within the bones of the skull, hepatosplenomegaly ensues, there is a delayed development of the endocrine organs including the sexual organs, and a progressive iron overload with secondary hemochromatosis.

There are two direct consequences of β-thalassemia. First, there is an inadequate formation of HbA and, therefore, an impaired ability to transport oxygen. There are also multiple effects attributable to an imbalance between α- and β-chain synthesis. Surprisingly, the pathological consequences of globin chain imbalance appears to be the more severe. Free α chains form unstable aggregates that precipitate within red cell precursors in the form of insoluble inclusions. These inclusions damage cellular membranes resulting in a loss of potassium. The cumulative effect of these inclusions on the red blood cells is an ineffective erythropoiesis. An estimated 70% to 85% of normoblasts in the marrow are eventually destroyed. Those that do escape immediate destruction are at increased risk of elimination by the spleen where macrophages remove abnormal cells. Further, hemolysis triggers an increased expression of erythropoietin which expands populations of erythroid precursors within bone marrow and leads to skeletal abnormalities. Another severe complication of β-thalassemia is that patients tend to have an increased ability to absorb dietary iron. As most treatments for thalassemia involve multiple transfusions of red blood cells, patients often have a severe state of iron overload damaging all of the organs and particularly the liver. To reduce the amount of iron in their systems, iron chelators are typically administered. Although helpful, patients succumb at an average of between about 17 to 35 years of age to the cumulative effects of the disease and iron overload.

Genotypic variations in healthy individuals have been identified wherein adult β-globin is not formed, but severe complications are avoided. These patients constituitively express fetal or γ-globin protein in amounts sufficient to substitute for the missing β-globin protein. This hereditary persistence of fetal hemoglobin (HPFH) may involve one or both of the fetal β-globin genes, A-γ and G-γ. Apparently, consistent production of either γ-globin protein accomplishes the necessary functions of the abnormal or missing β-globin protein.

A variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells. Additional studies showed that polar compounds, such as acid amides, and fatty acids could stimulate the expression of both fetal and adult globin genes in murine erythroleukemia cells. Hydroxyurea ($H_2NCONHOH$), another relatively small molecule, was found to stimulate globin expression. Stimulation, however, does not appear to be very specific to fetal globin. Hydroxyurea is currently the only drug used to treat sickle cell disease. However, there is great concern that an antineoplastic ribonucleotide reductase inhibitor is be carcinogenic, its carcinogenic properties make its widespread and long term use as a pharmaceutical a questionable practice. There is a strong need to find methods of treating sickle cell disease that do not include the patient's exposure to other risks.

Expression from the γ-globin genes has been successfully manipulated in vivo and in vitro using agents such as cytosine arabinoside (AraC), a cytotoxic agent that induces fetal reticulocyte production, and 5-azacytidine (AZA), a well-known DNA methylase inhibitor. Continuous intravenous administration of AZA produced a five- to seven-fold increase in γ-globin mRNA of bone marrow cells. Additional studies have shown that there are significant alterations in the population of stem cells in the bone marrow after AZA treatment. These experiments indicate that AZA's effects may be more attributable to reprogramming and recruitment of erythroid progenitor cells than to any direct effects on specific gene expression. Many of these agents including AZA, AraC and hydroxyurea are myelotoxic, carcinogenic or teratogenic making long-term use impractical.

One of the major breakthroughs in the treatment of hemoglobinopathies was made when it was discovered that butyric acid (butanoic acid; $CH_3CH_2CH_2COOH$) accurately and specifically stimulated transcription of the human fetal (γ) globin gene. These findings were quickly confirmed in vivo wherein it was shown that pharmacological doses of butyric acid greatly increased expression of fetal globin in adult chickens rendered anemic by injections with phenylhydrazine. It was speculated that histone acetylation, a known effect of butyric acid, may be at least partly responsible for increased fetal gene expression.

Over 50 derivatives of butyric acid have since been found to be effective in stimulating fetal globin production. Some of these include butyric acid salts such as sodium and arginine butyrate, α-amino-n-butyric acid (butyramide; $CH_3CH_2CH_2CONH_2$), and isobutyramide ($CH_3CH(CH_3)CONH_2$). Although promising in pilot clinical studies, treated patients were unable to maintain adequate levels of fetal globin in their system. It was later determined that many of these forms of butyric acid had extremely short-half lives. Oxidation in the serum, clearance by hepatocytes and filtration through the kidneys rapidly eliminated these agents from the patient's system. With others, patients rapidly developed tolerance or metabolites of compounds had the opposite of the desired effect.

Recently, a number of aliphatic carboxylic acids were tested for their ability to specifically increase fetal globin expression in K562 human erythroleukemia cells. Although longer chains were considered toxic to cells, propionate ($CH_3CH_2COOH$) and valerate (pentanoic acid; $CH_3CH_2CH_2CH_2COOH$) were found to be most effective. Butyrate ($CH_3(CH_2)_2COOH$), caproate ($CH_3(CH_2)_4COOH$), caprylate ($CH_3(CH_2)_6COOH$), nonanoate ($CH_3(CH_2)_7COOH$), and caprate ($CH_3(CH_2)_6COOH$) produced much less of an effect. Phenyl acetate ($C_6H_5CH_2COOH$) and its precursor, 4-phenyl butyrate ($C_6H_5CH_2CH_2CH_2COOH$), were found to decrease fetal globin expressing reticulocyte proliferation, but increase relative proportions of fetal globin per cell in cultured erythroid progenitor cells. Acetate ($CH_3COOH$), a metabolic product of butyrate catabolism, increased both erythrocyte precursor populations and also fetal globin synthesis. However, these studies also demonstrated that positive effects could only be maintained for very short periods of time.

Other methodologies to increase fetal globin expression have focused on recruitment and reprogramming of erythroid progenitor cells to express fetal globin. Agents tested in vivo or in vitro using this approach include hematopoietic growth factors such as erythropoietin (EPO), granulocyte/macrophage-colony stimulating factor (GM-CSF), and interleukin-3 (IL3). Each of these factors were found to increase fetal globin synthesis in tissue culture cells.

Other agents shown to affect fetal globin expression include activin and inhibin. Inhibin, a disulfide linked hormone of two subunits, suppresses secretion of follicle-stimulating hormone from the pituitary gland. Activin, sometimes referred to as erythroid differentiating factor (EDF) or follicle-stimulating hormone releasing protein (FRP), is also a hormone and both of these macromolecules induced hemoglobin accumulation in cultured human erythrocytes (S. P. Perrine et al., Blood 74:114a, 1989). Recently, studies have shown that steel factor, a product of the mouse steel locus, is also capable of influencing fetal globin synthesis in erythroid progenitors.

Several studies have focused on the mechanism whereby butyric acid and other small organic molecules have been able to stimulate fetal globin expression. Experiments with cells in culture have indicated that butyric acid may act by increasing the level of histone acetylation by, possibly, decreasing the activity of one or more histone deacetylase. Resulting histone hyperacetylation may produce nucleosome unfolding and thereby increased gene expression. Other studies have indicated that hypo-methylation of the area of DNA around the β gene complex correlates with increased γ-globin gene expression in thalassemic patients. Alternatively, butyric acid and other small molecules may function to increase specific gene expression by acting directly on agents which regulate transcription, the so-called transcription factors. These factors bind to sequence-specific sites along the genome at areas which control the expression of proximally located genes.

In contrast to the human a-globin gene locus, the β-locus has been analyzed in great detail due, in part, to the identification of multiple mutations of β-globin genes in HPFH patients. The β-locus contains a large upstream sequence referred to as the locus control region (LCR), extending 8-16 kbp 5' of the epsilon gene. This sequence is divided into four DNase hypersensitive sites, HSS 1-5, that contain enhancer sequences, silencer sequences, transcription factor binding sites and other cis acting sequences. Each of the genes of the β-globin cluster contains its own promoter which acts in concert with enhancer elements in the LCR. In fact, deletion of the LCR results in a thalassemic syndrome with little to no β-globin expression. These results indicate that the β-globin gene expressed may exert a competitive interaction over the LCR so that its enhancer effect is only available to a single gene at any given time of development.

A number of transcription factors have been identified in the β-locus which are thought to alter the level of β-globin gene expression. An enhancer element of the LCR has been shown to contain a pair of binding sites for nuclear factor E2 (NF-E2) which overlaps a tandem set of binding sites for transcription factor AP-1.NF-E2, a hematopoietic-specific basic leucine zipper protein, and AP-1 binding sites have been located on a variety of globin genetic elements. Recently, a conserved sequence (CS) located upstream of the AP-1/NF-E2 site has been proposed to augment enhancing activity.

Additional factors that bind to elements within the promoters of the β-globin cluster have been identified. The CAT box displacement protein (CDP) binds to the sequence CAAT, located about 50 bp upstream of many gene promoters. Another fairly ubiquitous transcription factor, SP1, binds to positions −140 and −202, and possible additional sites as well. TAFII110 has been shown to binds to the TATA box of many of the β-globin promoters. Transcription factor GATA-1, binds to the transcription initiation site (GATA) and may be displaced by TFIID when forming an active initiation complex. Another erythroid-specific factor, YY1, binds to at least 11 sites distributed throughout the globin regulatory region.

Recently, a factor has been identified that may be involved in the developmental regulation of hemoglobin expression. This factor, termed the stage selector protein (SSP), binds to a site located about 50-60 bps upstream of the gamma globin promoter referred to as the stage selector element (SSE). The SSE is also the site where a number of mutations have been found in HPFH syndrome patients. SSP has been purified from K562 cell nuclear extracts and its relatively fetal and erythroid specificity has been attributed to a heterodimeric partner protein of 40-45 kD termed CP2 which selectively allows assembly of the SSP complex on the SSE, and also on sites within the ε promoter, and subsequent interaction with RNA polymerase.

Elucidating the mechanism of developmental hemoglobin (Hb) switching may allow the reactivation of fetal Hb in adult humans with sickle cell disease or β-thalassemia, a manipulation that alleviates the clinical manifestations of these diseases. Inactivation of the mutated form of the adult β-globin gene that causes sickle cell disease is also of clinical value, since it results in a compensatory increase in γ(fetal)-globin expression.

It is clear that developmental regulation of globin genes involves multiple trans-acting factors, and the mechanism of switching is likely to require chromatin remodeling and interactions among protein factors bound at a variety of DNA regions. Although a few of the known DNA-binding proteins display some developmental specificity (e.g., erythroid Kruppel-like factor, EKLF, a positive regulator of the adult β-globin gene;(Donze, D., Townes, T. M. & Bieker, J. J. (1995) *J Biol Chem* 270,1955-9; and FKLF-2, which activates the γ globin genes, but also, to a lesser degree activates the ε- and β-globin genes—Asano, H., Li, X. S. & Stamatoyannopoulos, G. (2000) *Blood* 95, 3578-3584.), the precise combination of factors that mediate Hb switching and exactly how they do so are not clear.

Human K562 cells treated with hemin exhibit an Hb phenotype similar to embryonic erythroid cells, expressing primarily e- and g-globins but no adult β-globin, i.e., embryonic red cells of humans and other vertebrates also contain a large amount of ferritin of the specialized-cell (H) type (which stores iron for use by other cells, mainly), whereas erythrocytes of adults contain much less ferritin of the housekeeping type which stores iron for self/intracellular use.

After a long series of experimentation, the inventors discovered that in CV-1 cells, an expression clone of human H-ferritin down-regulates expression of an EKLF-stimulated β-globin promoter-driven CAT reporter gene. The inventors further show that ferritin in nuclear extracts of K562 cells can bind 5'-β-globin DNA between −153 and −148 and that a highly conserved hexanucleotide sequence CAGTGC is required for this binding. This sequence is essential for b-globin expression in DMSO-induced MEL cells (deBoer, E., Antoniou, M., Mignotte, V., Wall, L. & Grosveld, F. (1988) *Embo J* 7, 4203-4212) and is part of the binding site of a purported b-globin repressor in uninduced MEL cells (Macleod, K. & Plumb, M. (1991) *Mol Cell Biol* 11, 4324-32). When this CAGTGC motif is mutated, in vitro binding is reduced approximately twenty fold. The ability of ferritin-H to repress in this system is abolished, but EKLF-stimulation is retained, when the −153/−148 ferritin binding site is mutated in the co-transfected β-globin-reporter plasmid. These results show that ferritin H can repress the human adult β-globin gene by binding the promoter in a sequence-specific manner. The biology of this ferritin-family protein and its binding site, as well as its demonstrated function in transient assays, suggest that in K562 cells it is indeed functioning as a β-globin repressor. As noted above, such a repressor is useful in ameliorating sickle cell and other genetic diseases.

Studies have shown that ferritin-H exhibits the most efficient ferroxidase activity when it is expressed at roughly the same levels as ferritin-L. Equal expression levels result in the highest number of ferritin-H/ferritin-L heteropolymers. The heteropolymeric form of the 24-mer ferritin complex is the most efficient at converting the ferrous ion to the ferric ion and at sequestering iron ions. This suggests that maintaining equal concentrations of ferritin-H and ferritin-L is most likely to result in proper iron management. Increasing levels of ferritin-H would result in the formation of ferritin-H homopolymers. Ferritin-H homopolymers exhibit low ferroxidase activity. It would be expected that this would lead to higher levels of the more harmful ferrous ion and have adverse affects on the cells. However, the inventors have discovered that the gene regulatory functions of ferritin-H causes just the opposite to occur.

Background for skin cancer and other cancers:

Ultraviolet (UV) light is known to be damaging to human skin and has been implicated in the etiology of skin cancers. Recent studies have revealed that ferritin is elevated in cultured skin cells exposed to UV light, and it has been postulated that the increased ferritin represents the skin cell's attempt to protect itself from free radical damage by binding and sequestering iron which could, in turn, cause oxidative and free radical-mediated damage.

The rationale for other cancers is similar. Iron has been implicated as an etiologic or exacerbating agent in skin cancer, hepatomas (liver cancer), renal cell carcinoma (kidney cancer), neuroblastomas, leukemias, and breast cancer. The inventors propose that ferritin-H will be protective against carcinogenic events in cells that give rise to all of these cancers. The inventors' present rationale is that by treating human skin in such a way as to transfect them with a ferritin-H-subfamily peptide or gene that will express the peptide, protection from UV-induced damage can be provided to the cells. Ferritin-H-subfamily peptides are superior in this regard since they can sequester iron and not release it readily and can do so without altering normal aspects of the cells iron metabolism and other functions. Ferritin-L-subfamily peptides, on the other hand, are likely to cause even more harm in that they readily give up iron which would exacerbate the problem by increasing free iron and radical generation. Thus, delivering a ferritin-H-subfamily peptide or a gene (expression clone) for the peptide to the target cells would be protective and/or corrective of events that lead to cancer. Similarly, agents that would activate the endogenous ferritin-H-subfamily gene or genes would be beneficial in the same ways.

It is realized that all human ferritins, even those highly enriched in ferritin-L, require a small amount of ferritin-H and its associated ferrooxidase activity to carry out the functions of iron storage and release. It is the balance between ferritins L and H that is critical. Increasing the balance in favor of ferritin-H, even to the point of great excess of ferritin-H, appears to mediate a cell's return to healthy iron management Background for neurodegenerative diseases:

The distribution of free iron and of ferritin both change during brain development in animals and humans. Increased iron is found in the basal ganglia, beginning early in the disease process, in both Parkinson's disease and Huntington's disease. There is an increase in iron in several areas of the brain in Alzheimer's disease, in other dementias, and in aging; and the distribution of isoferritins in a variety of brain areas is different and changes in the above diseases. H-ferritin, but not L-ferritin, is present in the nucleus of neuronal cells in the cortex of developing rat brains and may be protective against oxidative damage that would be caused by free iron. Rationale: Ferritin-H decreases in critical brain cells during aging and neurodenerative diseases, whereas free iron and iron released from localized ferritin-L are implicated in oxidative damage in diseases and dementia. Ferritin-H or a related subfamily peptide will be protective against a variety of neurodegenerative changes associated with aging, the above diseases and dementias. Likewise, an expression clone of a ferritin-H-subfamily gene and/or a regulator of ferritin-H-subfamily genes, if delivered to the appropriate brain area and to specific cells, is predicted to be protective.

Background for Friedreich's ataxia and related neuromuscular disorders:

Deletion of YDL120, the yeast homologue of the human gene responsible for Friedreich's ataxia, elicits decreased cellular respiration associated with decreased cytochrome c oxidase activity and, in certain nuclear backgrounds, mitochondrial DNA is lost. In the null mutants, the cellular growth is highly sensitive to oxidants, such as H2O2, iron and copper; and ferrous sulfate elicits loss of mitochondrial DNA. Mitochondria of the null mutants contain ten times more iron than wild-type. The neurodegeneration observed in Friedreich's ataxia can be well explained on the basis of a mitochondrial iron overload responsible for an increased production of highly toxic free radicals. Rationale: Since iron accumulation is implicated in the etiology of Friedreich's ataxia, both the initial appearance of symptoms and the progression of this disease will be slowed or halted by sequestering the free iron. Transfection of ferritin-H-subfamily peptides or expression clones and/or treatment with agents that would up-regulate expression of the endogenous ferritin-H-subfamily genes will be ameliorative.

Background for atherosclerosis:

Strong epidemiological evidence is available that iron (i.e., iron excess) is an important factor in the process of atherosclerosis and that iron depletion has cardiovascular benefits and protects against ischemic heart disease. Iron-catalyzed generation of free radicals may contribute to vessel wall damage, to plaque formation and, by both mechanisms, to cardiac vessel damage. Once again, intracellular iron release from L-ferritin is implicated as a source of the iron contributing to this etiology; H-ferritin may be protective by chelating and sequestering the free and released iron. Rationale: Transfecting the appropriate cell with an ferritin-H-subfamily peptide or gene expression clone or with a gene regulator that will activate the endogenous ferritin-H-subfamily gene(s) in artery wall cells or cellular elements of athersclerotic plaques will prevent or reverse artery blockage.

Background regarding possible delivery systems and cell-targeting mechanisms:

For delivery of proteins or peptides into living cells ex vivo there are several approaches. Small peptides (about 20 kDa or smaller) may be taken up by cells without a specialized delivery system. Larger proteins may be delivered encapsulated into liposomes, liposomal constructs, or within a membrane such as a red cell ghost, and the vesicles are then made to fuse with the recipient cells by chemical means (e.g., polyethylene glycol [PEG] or calcium ions). Larger protein complexes may also be delivered encapsulated, by fusing the membranes of the capsule to the plasma membranes of the target cell. The inventors have had a large amount of experience with this type of delivery in the inventors' laboratory (references listed below). For in vivo delivery of proteins or peptides targeted to a specific cell type, the method of choice is likely to be a liposomal-type of delivery with an antibody or ligand directed at a specific cell surface protein or receptor incorporated into the liposome and the peptide or protein encapsulated within the liposome. Alternatively, a fusion protein comprised of the desired peptide (e.g., ferritin-H) fused with a protein ligand specific for the target cell receptor might be injected directly. An example of a protein ligand one might use to target hematopoietic stem cells is Stem Cell Factor (c-kit ligand) which binds to a receptor (c-kit) enriched on the surface of hematopoietic stem cells in the bone marrow. Those skilled in the art will recognize that there are a wide variety of pharmaceutical delivery mechanisms suitable for introducing proteins, protein fragments and genetic material into a cell.

For delivery of expression clones of genes encoding ferritin-H-subfamily peptides (for example), a number of plasmid carriers and transfection reagent systems are available to transfect cells ex vivo, to generate either stable transformants or transiently transfected cells, for reinfusion into the host animal or patient. Good expression plasmids are commercially available as are transfection reagents, many of the latter being cationic liposomes of one type or another. For in vivo as well as ex vivo gene transfer—that is, gene therapy—the vectors available include retroviral vectors (good only for dividing cells), adenoviral vectors (transfect many cell types, with very little cell specificity), adeno-associated viral vectors, lentiviral vectors, and electroporation systems. Any of these might be used in an ex vivo protocol where the target cells are obtained as a pure or highly enriched population, to be reinfused after gene transfer. For in vivo gene transfer, the choices are currently limited because of the difficulty of efficiently targeting specific cells with sufficient gene copies. A targeted liposome as described in the preceding paragraph is a possibility if a ligand for a high-affinity, plentiful but cell-specific receptor is incorporated.

Background regarding induction of ferritin-H gene expression in human cells:

Ferritin-H is among a group of genes that have been identified as being expressed during embryogeneis. The first major site of ferritin-H expression is in the embryonic red blood cell which is formed in the mammalian yolk sac before the blood circulation is established. This cell-specific expression of ferritin-H in early development corresponds to red cell's role as the iron storage site of the embryo. Adult red cells express much less ferritin, and iron is stored primarily in the liver (in hepatocytes) in adults where the primary ferritin expressed is ferritin-L. "Knocking out" the ferritin-H gene in mice results in intrauterine death between days 3.5 and 9.5 of development. Thus, ferritin-H is a developmentally regulated gene, expression of which is also somewhat restricted to certain cell and tissue types. The inventors have discovered that expression of ferritin-H in differentiating adult erythroid cells will reverse developmental hemoglobin switching, directly by repressing the adult β-globin gene, and either directly or indirectly causing an activation of the fetal gamma-globin gene. To activate endogenous ferritin-H gene expression in adult erythroid cells also reverses a developmental gene switch in this one cell lineage. Accomplishing this switch will, in turn, reverse another developmental switch, the hemoglobin switch, which has therapeutic benefits to people with sickle cell disease, β-thalassemia and other hemoglobinopathies. Activatinh ferritin-H expression in other cell types alleviates and protects against cancers, atherosclerosis, and neurodegenerative diseases.

It should be noted that although much is known about regulation of ferritin expression at the level of translation by iron as sensed by the IRE-binding proteins ( e.g., cytosolic cis-aconitase which is IRP-1 [IRE-binding protein-1]), this level and type of regulation does not distinguish between ferritin types. To specifically up-regulate ferritin-H expression requires regulation of the specific gene at the level of transcription.

BT-20 breast cancer cells rapidly increase ferritin-H mRNA synthesis when exposed to exogenously added heme but only slightly increase ferritin-L mRNA. This change is protective against the free radical damage of carcinogenesis. In colon cancer Caco-2 cells, ferritin-H expression leads to increased cell differentiation and a decline in the cancer phenotype. Increased ferritin-H expression also occurs during cell differentiation of erythroleukemia (K562) and hepatoma (HepG2) cell lines in culture. Although some of the DNA elements in the ferritin-H gene promoter and nuclear proteins that bind to them (e.g., P/CAF-CBP, Bbf, and NF-E2) are known, the mechanism of activation of ferritin-H transcription is not understood sufficiently to be applied clinically.

Among the exogenous factors that can be delivered/applied to cells to activate endogenous ferritin-H gene expression are heme, the phytohormone abscisic acid, and combinations of infrared and ultraviolet light, especially as applied to human keratinocytes and skin cancers.

SUMMARY OF THE INVENTION

The inventors have discovered that a nuclear ferritin-H subfamily of iron-sequestering proteins is a gene regulatory protein in human cells. Specifically, we have found that nuclear ferritin binds to a specific DNA sequence that is centrally placed in the promoter of the human β-globin gene and that the effect of the ferritin-H binding is to repress transcription of this gene in transfected cells. Thus, a ferritin-H gene or peptide targeted to the correct cells offers a cure for sickle cell disease in which the β-globin gene is mutated, as well as other genetic diseases where there is mismanagement of iron. Over expression of ferritin-H up to 500× in human cells is not harmful, does decrease the labile iron pool, decreases proliferation in cancer cell lines, and promotes apoptosis in cancer cells.

The present invention relates to a method and/or composition of altering the phenotype of a cell from the inside via producing a change in gene expression, i.e., gene expression therapy. Methods are described for transferring a gene for ferritin-H or other ferritin-H family peptides into a cell so that the ferritin-H gene is expressed therein and, as a result of this ferritin-H is produced. This alters the phenotype of the cell either through the ferritin itself regulating the expression of another gene associated with the disease phenotype (as in the inventors' well studied example of sickle cell disease) or through the ferritin changing the iron balance within the cell which, in turn, results in a change in gene expression that alters the phenotype. The phenotype of the effected cell can also be altered by delivering the expressed peptide itself (i.e., ferritin), or a part thereof, directly into the diseased cell or to the cell before it exhibits the disease phenotype. Induction of expression of the endogenous ferritin-H gene in the appropriate cells by stimulating its transcription is a third approach to gene regulation therapy; this will be done by applying to the cells exogenous cytokines or other agents. H-ferritin is known to increase in response to TNFα or IL-1β, whereas L-ferritin selectively increases in response to exogenously added iron. And a fourth approach is to alter the cell phenotype by gene regulation therapy by delivering an antisense oligonucleotide that would prevent expression of a specific ferritin family peptide by inhibiting translation and/or transcription of its mRNA.

Which of these approaches to gene regulation therapy will be applicable will depend on the etiology of each of the specific diseases described herein, all of which involve mismanagement of iron. Ferritin gene expression may either ameliorate or exacerbate depending on the type of ferritin expressed, on the specific disease, or the stage of disease at which intervention is initiated. The approach of choice may be to increase ferritin-H (e.g., by giving an expression vector of the ferritin-H gene) or to decrease a specific ferritin type (e.g., by an antisense oligonucleotide). Either of these approaches will achieve the desired effect. It is the balance between expression of ferritin-H and other ferritins that results in the cellular change in phenotype. Increasing the amount of ferritin-H in relation to the concentrations of the other ferritin proteins achieves the desired genetic regulation that ameliorates the effects of genetic diseases that cause the mismanagement of iron.

Delivering ferritin-H, a ferritin-H gene or derivatives thereof to erythroid precursor or stem cells represses expression of the mutated adult β-globin gene in sickle cell disease and concomitantly to stimulate γ(fetal)-globin gene expression thereby effecting a phenotypic cure.

In neurodegenerative diseases and neuromuscular disorders such as Alzheimer's disease (AD), Parkinson's disease (PD), Huntington's disease (HD), and Friedreich's ataxia, excess iron (or mismanagement of iron) is an etiologic or exacerbating agent. H-ferritin is selectively expressed in neurons and is also located in neuronal nuclei. H-ferritin declines in the brain with age and is low in particular brain regions in AD, PD, and HD. H-ferritin alone among the known ferritins possesses ferroxidase activity, and the presence of ferritin-H in the brain is protective against excess or free iron. Increasing H-ferritin in specifically localized neurons of this class of patients ameliorates the symptoms and progression of these diseases. Alternatively, the delivery of specific ferritin antisense oligonucleotides to glia and other associated CNS cell types in specific brain regions may be the preferred route of gene regulation therapy, as an approach to lowering levels of iron stores in such cells. Those skilled in the art will understand that the best method of increasing intracellular ferritin-H or a derivative thereof iron will depend on a variety of factors including, but not limited to, the type of tissue being targeted, the desired level of intracellular ferritin-H or derivative, the disease being treated and the current level of intracellular ferritin in the targeted cells.

In cancers, it is also clear that excess iron is involved as an etiologic or exacerbating agent. H-ferritin is known to be increased intracellularly in a number of cancers (e.g., breast cancer), whereas L-ferritin is increased in the serum of many cancer patients (e.g., neuroblastoma). The increase in H-ferritin expression seen in a number of cancers is the cell's attempt to protect itself against free/excess iron; and in such a case, very early delivery of H-ferritin, an H-ferritin gene, or stimuli to increase endogenous ferritin-H gene expression may be the best therapeutic choice. In skin cancer, where either UV or infrared light induce endogenous ferritin-H, the ferritin is protective against some routes of oxidative damage.

Excess iron in atherosclerotic plaques is an etiologic or exacerbating agent; and gene regulation therapy to increase ferritin-H in the cells of these plaques slows or halts the disease process.

An important aspect of the invention is the finding that ferritin-H represses the human adult β-globin gene by specifically binding the DNA sequence SEQ ID NO: 1, CAGTGC, in the β-globin promoter. Many other genes have this sequence in their promoters, including the human ε- and γ-globin genes that are stimulated by ferritin. Thus, the context of the CAGTGC motif, including the surrounding DNA as well as the distance of the motif from the start site of transcription, affects whether ferritin represses or activates. Some of the genes that have this promoter motif are expressed in apoptosis, and others are genes that are involved in iron metabolism. Using cytokines to push cancer cells into apoptosis is a route to a cure, and stimulating ferritin-H expression by this means is a powerful therapy.

The CAGTGC motif that we have discovered shares homology with important, previously discovered elements including the ARE (antioxidant response element) that has the sequence RTGACnnnGC (where R is a pyrimidine and n is any of the four standard nucleotides) and a sequence RTGR that is preferentially subject to cleavage by Fe++ mediated Fenton reactions. There are numerous other genes involved in health and disease that can be regulated through ferritin binding to these elements.

The above considerations have meaning as treatments because of the important discovery that nuclear ferritin (i.e., ferritin-H and derivatives thereof) represses gene expression from the human β-globin gene promoter by binding to the CAGTGC motif located in the region of –150 base pairs from the transcription start site, as shown by our in vitro DNA binding experiments and by our gene co-transfection experiments in CV-1 cells.

BRIEF DESCRIPTION OF THE DRAWINGS

FIG. 3A shows the 95 bp Rsa fragment (−222/−128) and two ds-oligos that overlap this same region (−164/−128 and −232/−188), that were each end-labeled and used as substrates for binding, using the antibody super-shift assay and crude K562 cell nuclear extract.

FIG. 3B shows a mobility shift assay. The super-shift band (arrow) was observed with the Rsa fragment and with the −164/−128 oligo, but not with the −232/−188 oligo, indicating that the binding site for nuclear ferritin is between −164 and −128 of the b-globin promoter.

FIG. 4A Shows sequences (SEQ ID Nos: 3-7) of wt and mutant oligonucleotides corresponding to the 5' binding region mapped in FIG. 3A. Mutated nucleotides and the original CAGTGC sequence are underlined. These oligos, used in the competitive gel shifts in FIGS. 4B, 4C, and 4D, were double-stranded; only the top strands are shown.

FIG. 4B shows competition gel-shift assays using the end-labeled wt sequence versus unlabeled wt or mutant no. 4 oligonucleotides, with partially purified ferritin-protein from K562 nuclei. Unlabeled oligonucleotides in the fold excesses shown were present with the labeled wt sequence at the time binding was initiated. Whereas the wt sequence competes significantly with itself at 50-fold excess, the oligonucleotide mutated in the CAGTGC sequence requires 1,000-fold excess to give the same level of competition. Labels: p, probe; sb, shift band; w, wells.

FIG. 4C shows the relative optical densities of the shift bands plotted versus molar excess of competitors, for the gel in FIG. 4B.

FIG. 4D Molar excesses of wt and mutant oligonucleotides required to produce 50% inhibition of binding of the labeled probe. Each mutant oligonucleotide required about the same molar excess as the wt sequence to produce 50% inhibition except mutant no. 4 (mutated in the 2153/2148 CAGTGC sequence), which required a 20-fold greater concentration to compete to the same ex-tent, indicating that CAGTGC is crucial for the DNA-protein interaction.

FIG. 5 shows a multiple sequence alignment of mammalian β-globin promoters, showing the high degree of conservation of the CAGTGC motif. Multiple sequence alignment of mammalian b-globin promoters (SEQ ID Nos: 8-19), showing the high degree of conservation of the CAGTGC motif. Promoter sequences (corresponding to −162/+1 of the human b-globin gene) were aligned for 12 mammalian species. GenBank accession nos. for the sequences are (from top down) V01317, X61109, X05665, X00376, M15387, X14727, M1740, J04429, Y00347, M11818, X15009, and X14061. Alignments were generated by using the programs PILEUP and LINEUP.

Gel shift detection of DNA looping before and after cutting the loop with restriction enzyme Sau 96I. The solid arrowhead marks the origin. Lane 1—migration of the pure 630 bp (−610/+20) DNA. Lane 2—DNA plus heated K562 nuclear extract, i.e., shifted DNA (DNA+protein). Lane 3—DNA plus heated extract, cut with Sau 96I. Lane 4—lane 2 sample, deproteinized before electrophoresis. Lane 5—lane 3 sample, deproteinized after cutting but before electrophoresis. Lane 6—DNA alone, precut with Sau 96I. Lane 7—DNA precut with Sau 96I, then reacted with extract proteins. (Note: Half as much material was loaded onto the gel for lanes 6 and 7, although the reaction conditions and concentrations were the same as lanes 1-5.)

Figure 1:
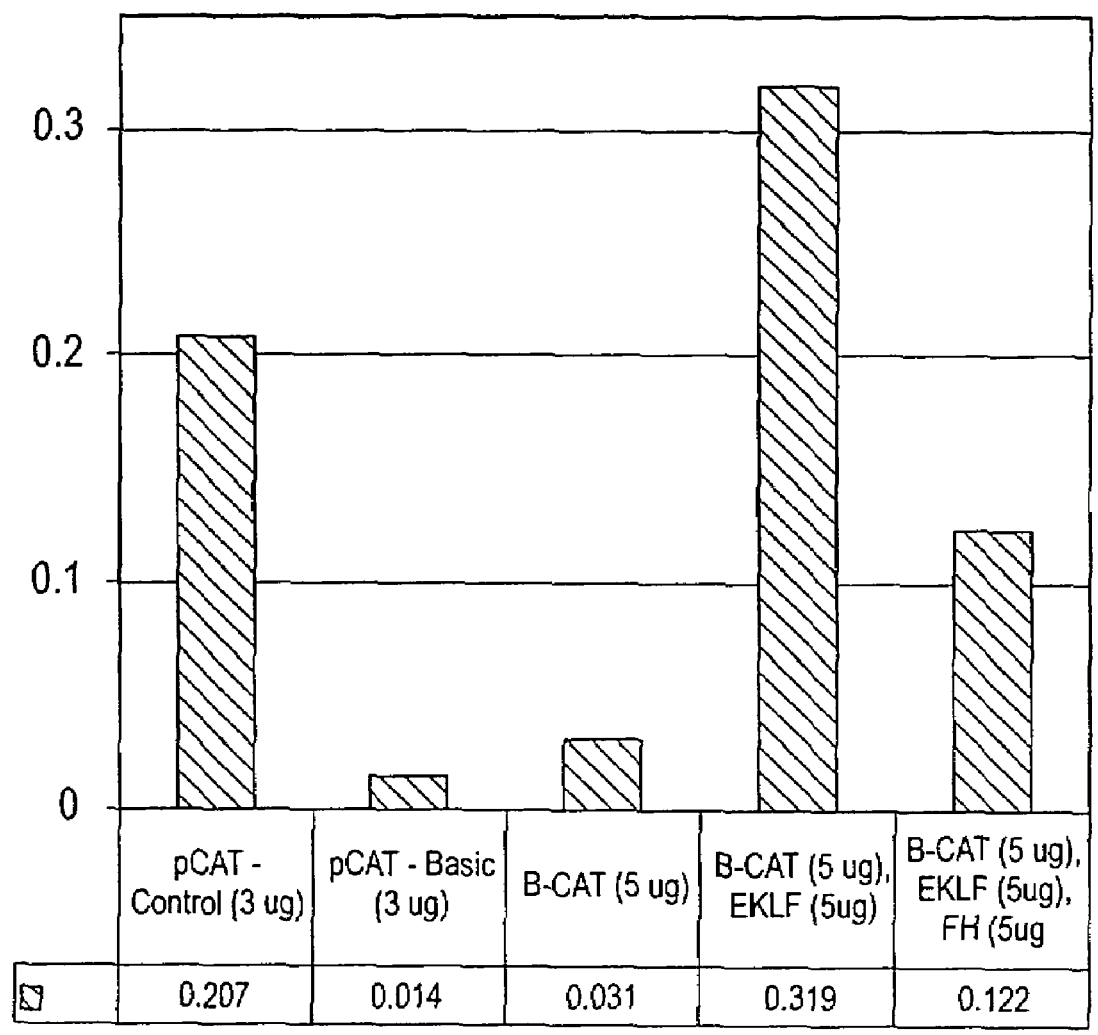
FIG. 1 shows Ferritin-H repression of the b-globin promoter in co-transfected CV-1 cells. Transient expression of a reporter gene encoding chloramphenicol acetyl transferase (CAT), expressed as ng CAT/mg cellular protein measured by an ELISA as described under Materials and Methods, is shown for CV-1 cells transfected with the following CAT plasmids (from left to right): CAT driven by an activated SV40 promoter (pCAT-Control vector), CAT plasmid with no promoter (pCAT-Basic vector), the non-stimulated human b-globin promoter (B-CAT), the b-globin promoter stimulated by a co-transfected EKLF effector plasmid (B-CAT, EKLF), and EKLF-stimulated b-globin promoter co-transfected with a ferritin-H expression plasmid (B-CAT, EKLF, FH). The reporter gene expression was repressed 62% by the presence of the co-transfected ferritin-H expression vector.
Figure 11:
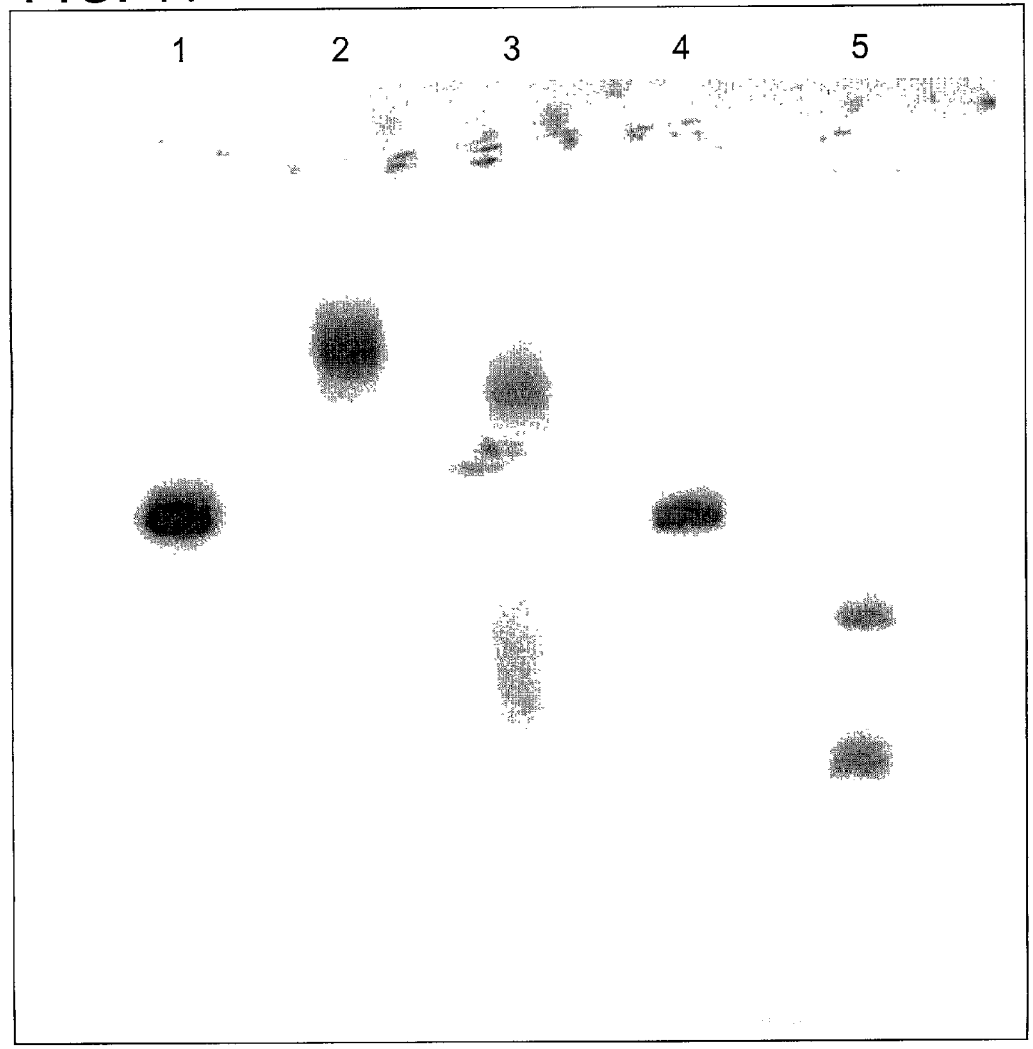

FIG. 11 The in vitro DNA looping assay, based on the combined use of the electromotive mobility shift assay (EMSA) and a single-site cleavage with an appropriate restriction enzyme. Lane 1: Migration of the 630 bp of 5' β-globin DNA alone (arrowhead marks the origin). Lanes 2 and 3: Gel shifts (EMSAs) were performed with a partially purified nuclear extract from uninduced K562 cells and the DNA, before (lane 2) and after (lane 3) cutting with Sau 96I. All the DNA was bound by protein in a single, shifted complex (lane 2) which retained its migration as a single band after the restriction cut (lane 3). Lanes 4 and 5: DNA samples recovered after deproteinization of the complexes in lanes 2 and 3, respectively. Preparation of nuclear extracts: Nuclear extracts of nonadherent K562 cells were prepared by the procedure of Dignam et al. as previously described. Partially purified extracts, 80% enriched in binding proteins of interest, were prepared by heating the nuclear extracts at 80° C., centrifuging, and retaining the supernatant fluid, as described by Atkinson et al. (25). The enriched extract contained proteins that bound the −150 (−164/−128) and the −530 (−584/−527) oligonucleotides in the standard EMSA. Gel mobility shift assays (EMSAs): The procedure of Fried and Crothers (26) was used, as described by Berg et al. (19), except that each reaction (which contained 2 ng [9,000 cpm] of 630 bp DNA, 2.5 ug of extract protein, 1.0 ug of poly dI:poly dC, 100 mM KCl, and binding buffer) was in a volume of 5 µl (instead of the usual 25 µl). The protein and DNA were allowed to interact at rm temp for 20 min. and the retardation assays were performed with four percent acrylamide gels at ionic strength. Design of DNA looping experiments: To detect looping due to the interaction of promoter-bound protein with protein bound further upstream (ca. −300 to −600 bp), the DNA-protein complex was reacted with Sau 96I, which cleaves this DNA at −210/−209 bp as shown in FIG. 1, using the manufacturer's instructions, modified as follows: 2 µl of enzyme and 15 µl of enzyme buffer plus BSA were used in a total volume of 31 µl which included the contents (5 µl) of the protein-DNA binding reaction, at rm temp.

Figure 12:
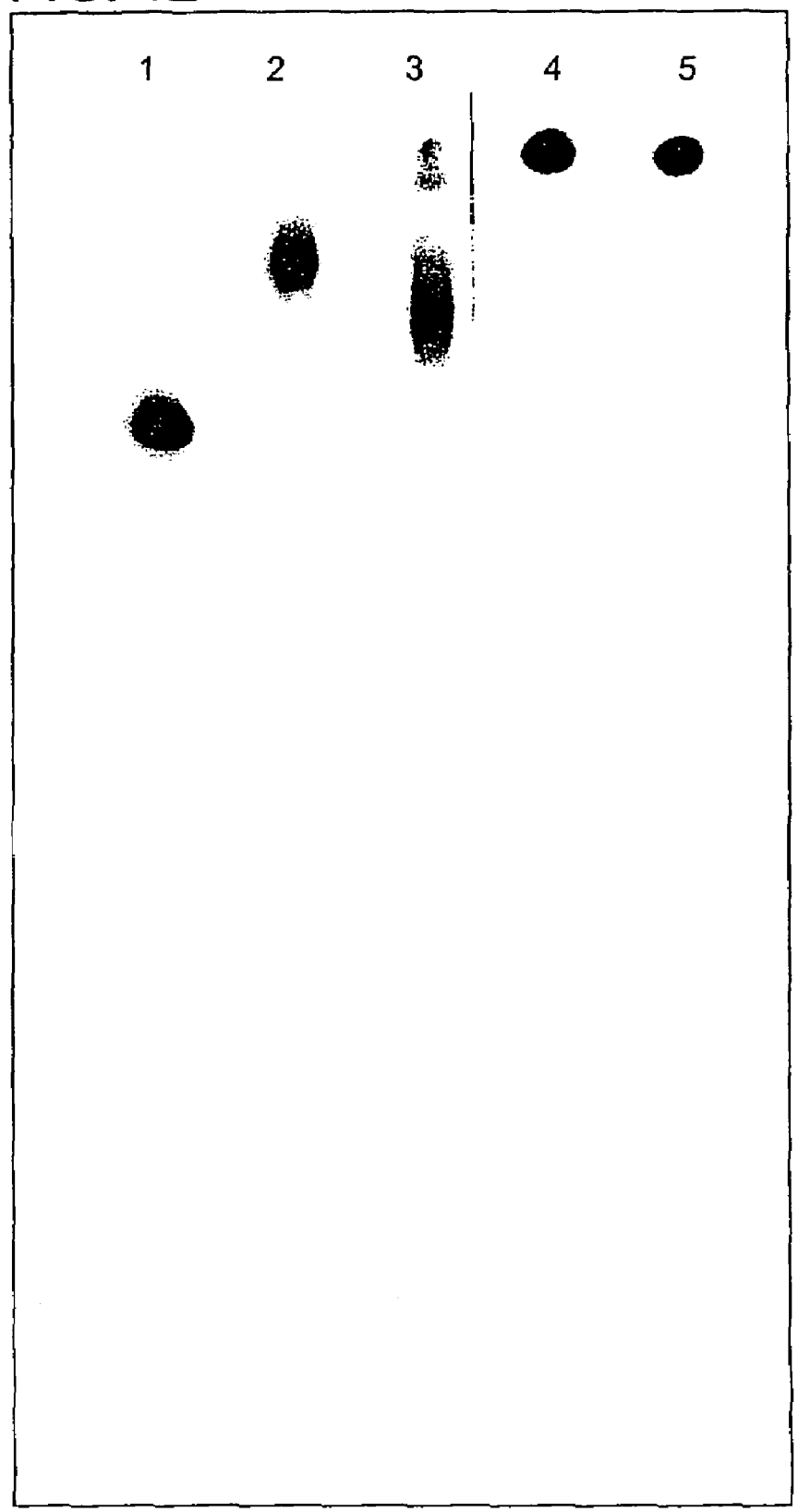

FIG. 12 shows a gel mobility shift assay showing that the nuclear extract contains a DNA binding protein that binds upstream of the ferritin-H binding site and also binds to ferriting. Lane one shows the unshifted 630 bp segment of the beta-globin 5' promoter region. Lane 2 contains the 630 bp fragment with nuclear extract added. Because both the upstream binding protein and ferritin-H are present, the DNA is looped and the band has shifted. Lane 3 contains the 630 bp fragment and nuclear extract from which the ferritin-H has been removed. Because only the upstream binding protein is present, there is less of a band shift. However, the fact that there is a lesser shift shows that a protein is bound, and that the complex is not as great due to the absence of ferritin-H. Lanes 4 and 5 have the same sample as lane 2 with anti-ferritin antiserum added. Because the 630 bp fragment is bound to the ferritin which then binds to the antiserum, a supershift results.

DETAILED DESCRIPTION OF THE INVENTION

It has been found that ferritin is a repressor of the human β-globin gene, the same gene that is mutated in sickle cell disease and in some forms of β-thalassemia. The repressor is a nuclear form of ferritin (Broyles et al., "A Ferritin-Like Protein Binds to a Highly Conserved CAGTGC Sequence in the β-globin promoter, In *Sickle Cell Disease and Thalassaemias: New Trends in Therapy*, of the ferritin H subfamily of ferritin peptides. Briefly, the inventors have found the following:

1) A ferritin-family protein from human K562 erythroleukemia cell nuclear extracts (as well as pure human ferritin-H) binds to the promoter of the human β-globin gene (the promoter that drives the mutated form of the gene in sickle cell) at −150 bp from the transcription start site, in vitro. The binding is very specific to that DNA sequence.

2). An expression clone of ferritin-H represses this β-globin promoter in transient co-transfection experiments. This is very reproducible in multiple experiments with two different reporter genes, with no repression seen by control/null plasmids.

3) Ferritin-H no longer represses if the promoter contains a mutated binding site. The inventors have a perfect control plasmid—a β-globin promoter mutated only in the ferritin-H binding site and hooked to the same reporter gene (CAT, in this case). This is not only the perfect control for the transfections, but it also connects the in vitro DNA binding with in vivo function quite nicely.

Since a decrease in β-globin expression is compensated by an increase in gamma (fetal)-globin expression in human erythroids cells, and since a modest amount of this switching is known to totally ameliorate sickle cell and wholly or partially ameliorate β-thalassemias, this new finding makes ferritin useful for curing the phenotype of these classic genetic diseases.

Reports in the scientific literature indicate that H ferritin (heavy chain ferritin) is decreased by 50% in aged rat brains and in other neurodegenerative diseases such as Alzheimer's and show that ferritin-H is found in the neurodegenerative diseases where iron-mediated oxidative damage has been demonstrated, as in Parkinson's disease and possibly Huntington's disease. There are also studies that indicate a protective role of ferritin against cancers, such as liver and skin cancers. It has been reported that UV light induces ferritin production in skin cells and that ferritin is protective against UV damage. Indeed, ferritin H can be used to treat any diseases in which cellular injury is caused by iron-mediated oxidative damage.

Delivering the ferritin-H peptide or a truncated form of it to erythroid precursor cells is a more effective, more natural form of therapy than the partial measures currently in use to treat sickle cell disease and β-thalassemias. Similar delivery of ferritin-derived peptides provides effective treatments and protection in Alzheimer's and other neurodegenerative diseases and cancers. The peptide can also be delivered as a fusion protein, with parts or all of the ferritin-H peptide fused to another protein such as transferrin or other ligand for which specific receptors exist on the surface of erythroid precursor cells, neurons, or other cell types for which protection is desired. The making of fusion proteins targeted to specific tissues is well know to those skilled in the art. Alternatively, an expression clone that encodes ferritin-H or a part of it, delivered to erythroid precursor cells, to hematopoietic stem cells, to neurons or to other tissue cells in an appropriate vector, either ex vivo or in vivo; and the protein expressed from such a vector also cures and protects against disease.

The ferritin-H described here is distinct from other known trans-acting proteins in its physical properties and its proposed function as a repressor that binds primarily to the β-globin promoter. The H-ferritin subfamily is represented by a larger number of genes than the L-ferritin subfamily and includes a cluster of genes/pseudogenes on the X chromosome. One of these, ferritin-X, appears to encode a peptide identical in size and very similar in predicted three-dimensional structure to ferritin-H.

The possibility remains that the actual DNA-binding of the b-globin promoter −150 CAGTGC motif is mediated in vivo by a ferritin-associated protein that would be protected from proteinase K and heat treatments and react with anti-ferritin antisera because of its strong association with ferritin. However, if this is the case, it is a protein that is ubiquitous in human nuclear extract and there would be no need to upregulate it and it is ineffective in the absence of ferritin-H. Upregulation of ferritin-H is enough.

Figure 6:
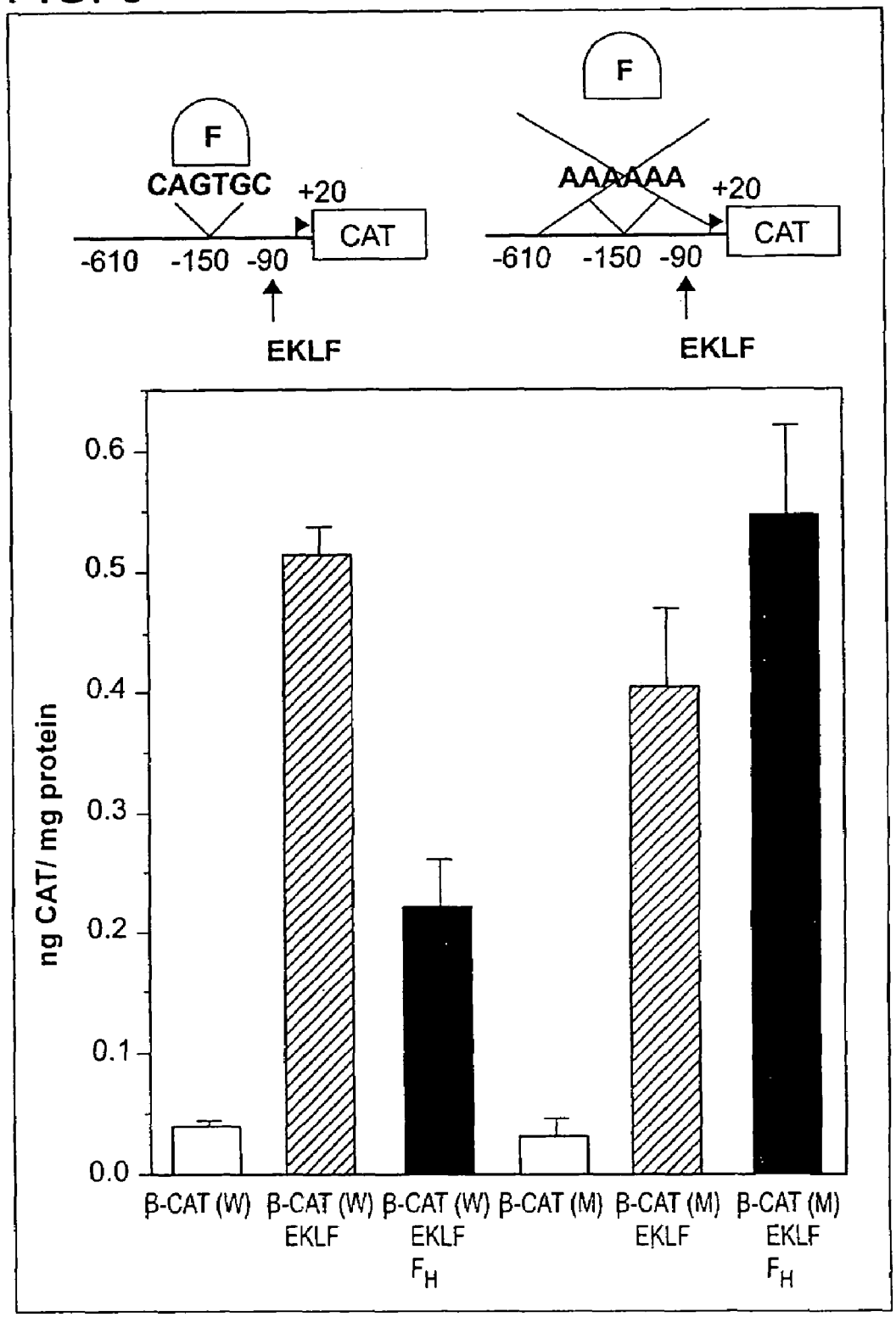
FIG. 6 shows co-transfection experiments demonstrating that ferritin-H losses its ability to repress if the b-globin promoter contains a mutated ferritin binding site. Cotransfection experiments demonstrating ferritin-H repression of the b-globin promoter and loss of ability to repress when the ferritin binding site (CAGTGC) is mutated. Transfections of CV-1 cells were performed with a constant amount (6 mg) of total plasmid DNAs mixed with 8 ml of DMRIE-C added to 2 3 10 6 CV-1 cells, such that each transfection had 2 mg ofb-CAT plasmid (W 5 wt, or M 5 mutant), 61 mg of EKLF, 63 mg of FH (ferritin-H expression plasmid), with the difference made up to 6 mg with pEGFP. Re-porter gene activity, expressed as ng of CAT per mg of cellular protein (measured by ELISA), is shown for the following combinations with either native (W) or mutant (M) b-CAT plasmids: the non-stimulated human b-globin promoter (open bars); the b-globin promoter stimulated by a cotransfected EKLF effector plasmid (hatched bars); and EKLF-stimulated b-globin promoter cotransfected with a ferritin-H expression plasmid (solid bars). (n 5 3 transfections per data set; bars 5 SEM). Construction of reporter plasmids (diagrammed above the histogram) is described below.

From the inventors' transient expression assays, it is clear that ferritin-H can repress the human b-globin gene and that this repression is mediated by binding of ferritin-H and/or a co-repressor to the −150 region of the promoter containing a highly conserved CAGTGC motif (FIGS. 1 and 6). The binding site of this ferritin-H is within an important ARE required for activation of transcription of the β-globin gene. Thus, the binding of this protein and displacement of other factors could be important in the repression of the human β-globin gene as apparently the mouse BB1 protein (which recognizes the same sequence) is in the repression of the mouse β-major globin gene in uninduced MEL cells. Subsequent interaction of this binding site with upstream negative regulatory regions creates a tightly-bound complex that prevents binding of other positive factors such as GATA-1 as well as sterically hinder the formation of an active transcription complex on the proximal promoter, by DNA looping.

Figure 7:
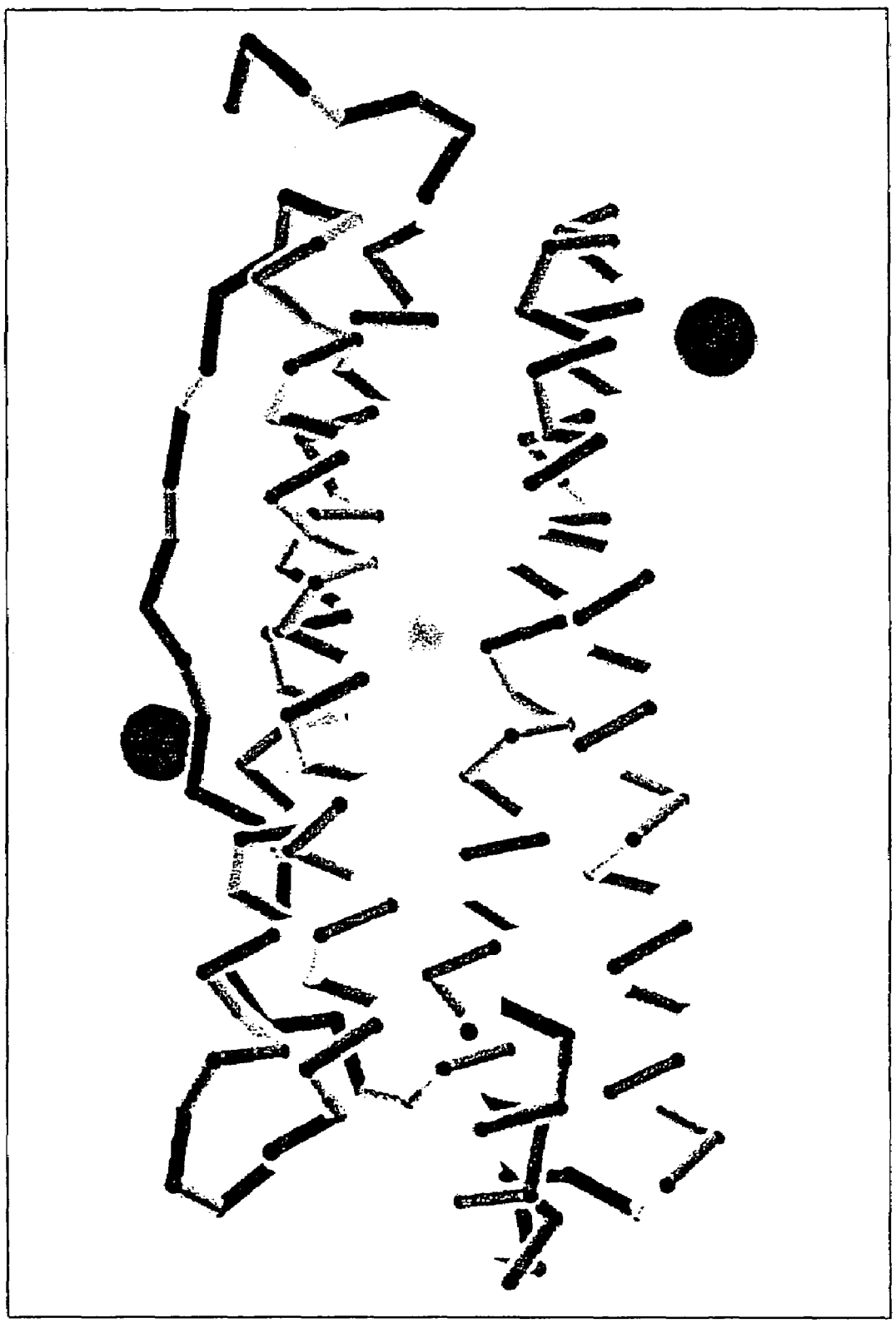
FIG. 7 shows a schematic representation of the Ferritin-H protein monomer having an iron ion bound to the ferroxidase active site (center). The two dark/solid circles at the periphery represent calcium ions.

FIG. 7 shows a schematic representation of the Ferritin-H protein having a bound iron ion. The active site responsible for ferroxidase activity has been elucidated. However, the active site or sites the protein responsible for transcription repression has not been identified. As with all other gene regulation proteins, derivatives of Ferritin-H will repress DNA transcription as well as or better than Ferritin-H itself. These derivatives include fragments of Ferritin proteins and any fusion proteins into which the active site or sites of Ferritin H responsible for transcription repression has been spliced. Ferritin H derivatives may also include larger transcription or translation products of a Ferritin family protein. Ferritin-H derivatives further include any mimetic proteins that represses DNA transcription by means of an active site that is substantially the same as the Ferritin-H active site responsible for DNA binding and transcription repression. Those skilled in the art will appreciate that the ferritin active site or sites responsible for repression of DNA transcription may include both DNA binding and protein binding sites. Ferritin-H derivatives may be found in fragments of any of the ferritin family proteins.

Ferritin H is only one member of the family of Ferritin proteins. Ferritin H and Ferritin L are the most studied. There are likely to be Ferritin family proteins that have not yet been identified. Ferritin family proteins are generally involved in iron metabolism. Now that the inventors have elucidated the gene regulatory activity of Ferritin H and its derivatives, it is likely that other Ferritin family proteins will also have gene regulatory functions.

The ability of Ferritin family proteins to bind to the 5' promoter region of the beta globin gene was ascertained only after lengthy and rigorous experimentation as described below. The first example shows that Ferritin-H binds to the CAGTGC ferritin binding site, SEQ ID NO: 1, found at bases −148 to −153 of the 5' promoter region of the human beta-globin gene. Example 2 shows that in addition to binding to the ferritin binding site, ferritin-H binds to another nuclear protein that binds to the beta-globin 5' promoter region further upstream of the ferritin binding site. FIGS. 8 through 12 show the experiments directed toward elucidating the mechanism by which ferritin-H represses the human beta[Greek symbol]-gene. These results represent work-in-progress and show that human K562 cell nuclear ferritin interacts with other DNA-binding proteins to repress this promoter, especially upstream silencer-binding proteins via DNA-looping."

EXAMPLE 1

Materials and Methods

Cell lines. K562 (human erythroleukemia) cells were grown in suspension in RPMI 1640 medium with 10% or 15% fetal bovine serum (FBS) and antibiotics as described (Berg, P. E., Williams, D. M., Qian, R. L., Cohen, R. B., Cao, S. X., Mittelman, M. & Schechter, A. N. (1989) *Nucleic Acids Res* 17, 8833-52) and harvested at a density of $10^6$ cells/ml for making nuclear extracts. CV-1 (African green monkey kidney epithelial) cells (adherent cells used for transfections/transient gene expression assays) were grown in DMEM with L-glutamine, 10% FBS and antibiotics (Miller, I. J. & Bieker, J. J. (1993) *Mol Cell Biol* 13, 2776-86).

Clones, transfections, and gene expression assays. The upstream region (−610/+20) of the human b-globin gene, previously cloned in pSV2CAT (Berg, P. E., Williams, D. M., Qian, R. L., Cohen, R. B., Cao, S. X., Mittelman, M. & Schechter, A. N. (1989) *Nucleic Acids Res* 17, 8833-52), was subcloned through pGEM and pSELECT (now called pAL-TER) and recloned into pCAT-basic (all vectors from Promega). Mutants of the −153/−148 site of the b-globin promoter were generated by transcription from mutant oligonucleotides corresponding to the −164/−128 region using the pSELECT system. Transfections of CV-1 cells were carried out with DMRIE-C transfection reagent (GibCo/BRL) in OptiMEM serum-free medium and were optimized using the green fluorescent protein plasmid pEGFP-C1 (Clontech), fluorescence microscopy and quantitative fluorescence of cell lysates with a microtiter plate reader. The reporter gene chloramphenicol acetyl transferase (CAT) was quantified in lysates of transfected cells using an ELISA (Promega) standardized with purified CAT. The EKLF (erythroid Kruppel-like factor) expression plasmid has the EKLF gene cloned into pSG-5 (Stratagene;( Miller, I. J. & Bieker, J. J. (1993) *Mol Cell Biol* 13, 2776-86) and the ferritin-H expression clone is in the eucaryotic expression vector pcEXV-1 (Wu, Y. J. & Noguchi, C. T. (1991) *J Biol Chem* 266, 17566-72). Total cellular protein was determined with the BCA microtiter plate assay (Pierce) using bovine serum albumin as a standard.

Proteins and antibodies. Ferritins from human liver (enriched in L chains) and from human heart (enriched in H chains), human transferrin (iron saturated) and apotransferrin, polyclonal (rabbit) antiserum to human spleen ferritin and nonimmune rabbit serum were obtained from Sigma Chemical Company.

Restriction fragments and oligonucleotides. The 5' region of the human b-globin gene (from −610 to +20), previously cloned in pSV2CAT, was cut into three fragments by sequential digestions with Hind III and Rsa I. The three fragments, electroeluted from agarose (Maniatis, T., Fritsch, E. F. & Sambrook, J. (1989) *Molecular Cloning: A Laboratory Manual* (Cold Spring Harbor Laboratory, Cold Spring Harbor, N.Y.), were 416 bp (−638/−223), 147 bp (−127/+20, containing the proximal promoter region), and 95 bp (the Rsa fragment, −222/−128, containing mainly distal promoter sequences). The three fragments were phenol/chloroform treated, dephosphorylated, and end-labelled with 32-P as described (Maniatis, T., Fritsch, E. F. & Sambrook, J. (1989) *Molecular Cloning: A Laboratory Manual* (Cold Spring Harbor Laboratory, Cold Spring Harbor, N.Y.; Kurien, B. T., Scofield, R. H., & Broyles, R. H. (1997) *Anal Biochem* 245, 123-126). Synthetic oligonucleotides corresponding to −232/−188 and −164/−128 were purified and annealed as previously described (Berg, P. E., Williams, D. M., Qian, R. L., Cohen, R. B., Cao, S. X., Mittelman, M. & Schechter, A. N. (1989) *Nucleic Acids Res* 17, 8833-52), and the double-stranded oligos were end-labeled as above and/or used as unlabeled competitors in gel mobility shift assays.

Preparation of nuclear extracts. Each nuclear extract preparation was made from two liters of K562 cells ($1 \times 10^6$ cells/ml) using the procedure of Dignam, Lebovitz, and Roeder (Dignam, J. D., Lebovitz, R. M. & Roeder, R. G. (1983) *Nucleic Acids Res* 11, 1475-89). Protein content of the extracts ranged from 3 to 6 mg/ml. Extracts enriched 80-90% in ferritin-like protein(s) were prepared by treating the crude extracts with proteinase K and/or heat at 75° C. (Atkinson, B. G., Dean, R. L., Tomlinson, J. & Blaker, T. W. (1989) *Biochem Cell Biol* 67, 52-7).

Gel mobility shift assays. Gel retardation assays (i.e., gel shifts) were used to determine DNA binding of the extract proteins to the Rsa I (95 bp) fragment and synthetic oligonucleotides (Berg, P. E., Williams, D. M., Qian, R. L., Cohen, R. B., Cao, S. X., Mittelman, M. & Schechter, A. N. (1989) *Nucleic Acids Res* 17, 8833-52; Fried, M. & Crothers, D. M. (1981) *Nucleic Acids Res* 9, 6505-25). Each reaction contained 0.5-2 ng of DNA, 1.0-5.0 ug of extract protein, 1.0-5.0 ug of poly dI:poly dC, 100 mM KCl, and binding buffer (Berg, P. E., Williams, D. M., Qian, R. L., Cohen, R. B., Cao, S. X., Mittelman, M. & Schechter, A. N. (1989) *Nucleic Acids Res* 17, 8833-52). Unlabeled competitor oligonucleotides ranged from 15- to 2000-fold molar excess and were included in the reaction mixture with the probe before adding protein. Gels used for retardation assays were 4%, 5%, or 6% acrylamide and the running buffer was low ionic strength TAE (Berg, P. E., Williams, D. M., Qian, R. L., Cohen, R. B., Cao, S. X., Mittelman, M. & Schechter, A. N. (1989) *Nucleic Acids Res* 17, 8833-52).

Sequence alignments and homology searches. All mammalian β-globin promoter sequences (−200/+1) were obtained directly from GenBank and manipulated using the PILEUP program followed by the LINEUP program of the University of Wisconsin GCG Package.

Results

Ferritin-H represses expression driven by the b-globin promoter in transient co-transfection assays. A transient expression assay was set up with CV-1 cells in which b-globin promoter-driven expression of a reporter gene is low unless the cells are co-transfected with an expression clone of EKLF, a developmentally-specific activator of transcription. Results with a b-CAT reporter plasmid are shown in FIG. 1. The expression level of b-CAT stimulated by EKLF was repressed by over 60 percent by co-transfection of an expression clone of human H-chain ferritin (i.e. ferritin-H).

Controls included a positive CAT-control plasmid (expresses CAT constituitively), a negative CAT-basic plasmid (contains no promoter), and b-CAT without EKLF stimulation. The experiment shown in FIG. 1 has been repeated five more times with b-CAT and three times with a b-Luc (b-promoter-luciferase) construct with very similar results. The repression is also evident (although reporter activity is lower) when EKLF is omitted (data not shown). Other controls have included co-transfection of the "empty" carrier plasmids for all the expression clones (no effect on reporter gene expression) as well as keeping the total amount micrograms of transfected DNA constant (e.g., FIG. 6), to rule out the possibility of non-specific inhibition of gene expression due to excess DNA or to some aspect of the structure of a carrier plasmid. Co-transfection of an expression clone for ferritin-L sometimes resulted in some repression of reporter gene expression; but the effect was less dramatic and inconsistently observed.

Figure 2A:
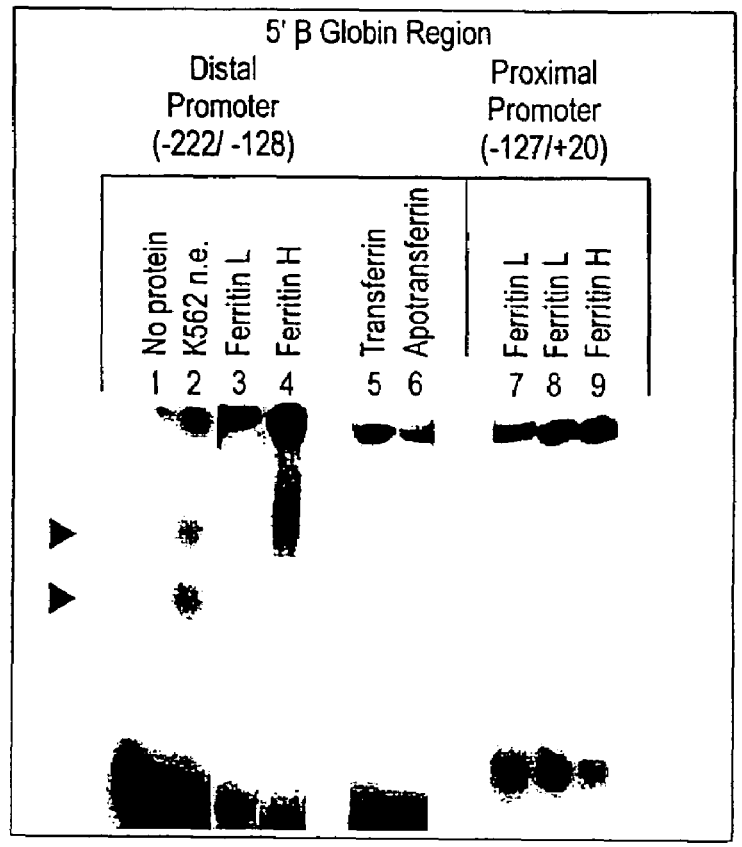
FIG. 2A shows the binding of ferritin chains to the distal promoter of the human β-globin gene. Restriction fragments of the 5'β-globin distal promoter (–222/–128), in the left side set of lanes 1 through 6, or proximal promoter (–127/+20), in the right side set of lanes 1 through 5, were end-labeled with $^{32}P$ and used as probes in gel mobility shift assays with K562 nuclear extract (left lane 2), purified human liver ferritin ($F_L$, lanes 3 [left] and 2, 3, and 4 [right]), human heart ferritin ($F_H$, lanes 4 [left] and 5 [right]), human transferrin (T, lane 5[left]) and apotransferrin (aT, lane 6[left]), as described under Materials and Methods. Lanes 1 [left and right] contained only DNA (no protein).
Figure 3A:
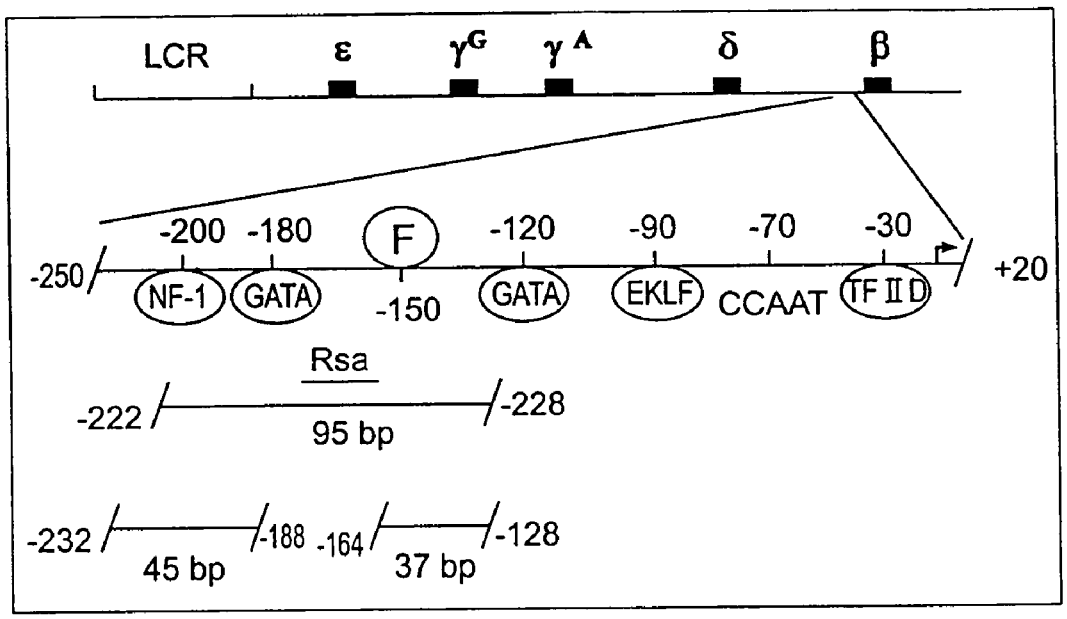
FIG. 3A-3B Localization of the binding region of nuclear ferritin to the −164/−128 region of the b-globin promoter, using the antibody super-shift assay.

Binding of ferritin to b-globin promoter DNA. A restriction fragment containing part of the distal promoter of the human β-globin gene, from −222/−128, is bound by human liver- or human heart-derived ferritin, as shown in gel retardation assays (FIG. 2a, left side, lanes 3 and 4). In the inventors' experiments, ferritin from human heart (which is enriched in H-type (heavy) subunits) showed a higher degree of binding than liver ferritin (which is relatively enriched in L-type subunits), as indicated by the darker band in lane 3 (left). A restriction fragment containing the proximal promoter (−127/+20) does not show this binding (FIG. 2a, right side, lanes 2-5); and another iron-binding protein, transferrin (known to be primarily extracellular except when bound to its receptor) does not bind the distal fragment bound by ferritin (FIG. 2a, left side, lanes 5 and 6). The shift bands produced by the binding of human liver ferritin and by human heart ferritin usually correspond to the lower and upper shift bands produced by K562 cell crude nuclear extracts, respectively (FIG. 2a, left side, lanes 2-4). The inventors have also found that nuclear extract ferritin can produce either shift band and that the higher molecular weight band will yield the lower band when eluted and reshifted. Multiple shift bands with crude extracts (e.g., FIG. 3) are the result of different sized aggregates of ferritin subunits or oligomers of the DNA-protein complex and/or complexes with other proteins in crude extracts, since the inventors have found that at least one of the multiple bands contains GATA-1.

Figure 2B:
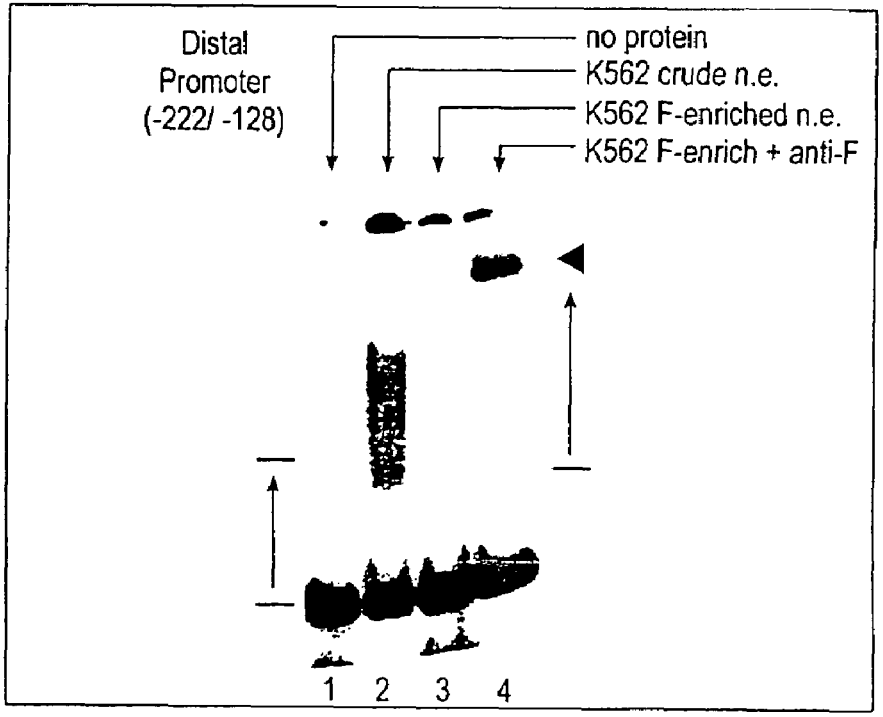
FIG. 2B shows the Binding of a ferritin-like protein from K562 cell nuclear extracts to –222/–128 β-globin region. A procedure for obtaining ferritin 90% pure from embryonic red cells using proteinase K digestion followed by heat treatment at 75° C. (36) was applied to K562 cell nuclear extract; the clear supernatant fluid obtained after centrifugation gave a singe shift band (third lane from left) which gave a "supershift" with anti-ferritin polyclonal antiserum (last lane), indicating that there is a protein in the nuclear extract with three properties of ferritin (proteinase K-resistance, heat stability, and reactivity with an antiferritin-specific antserum).
Figure 2C:
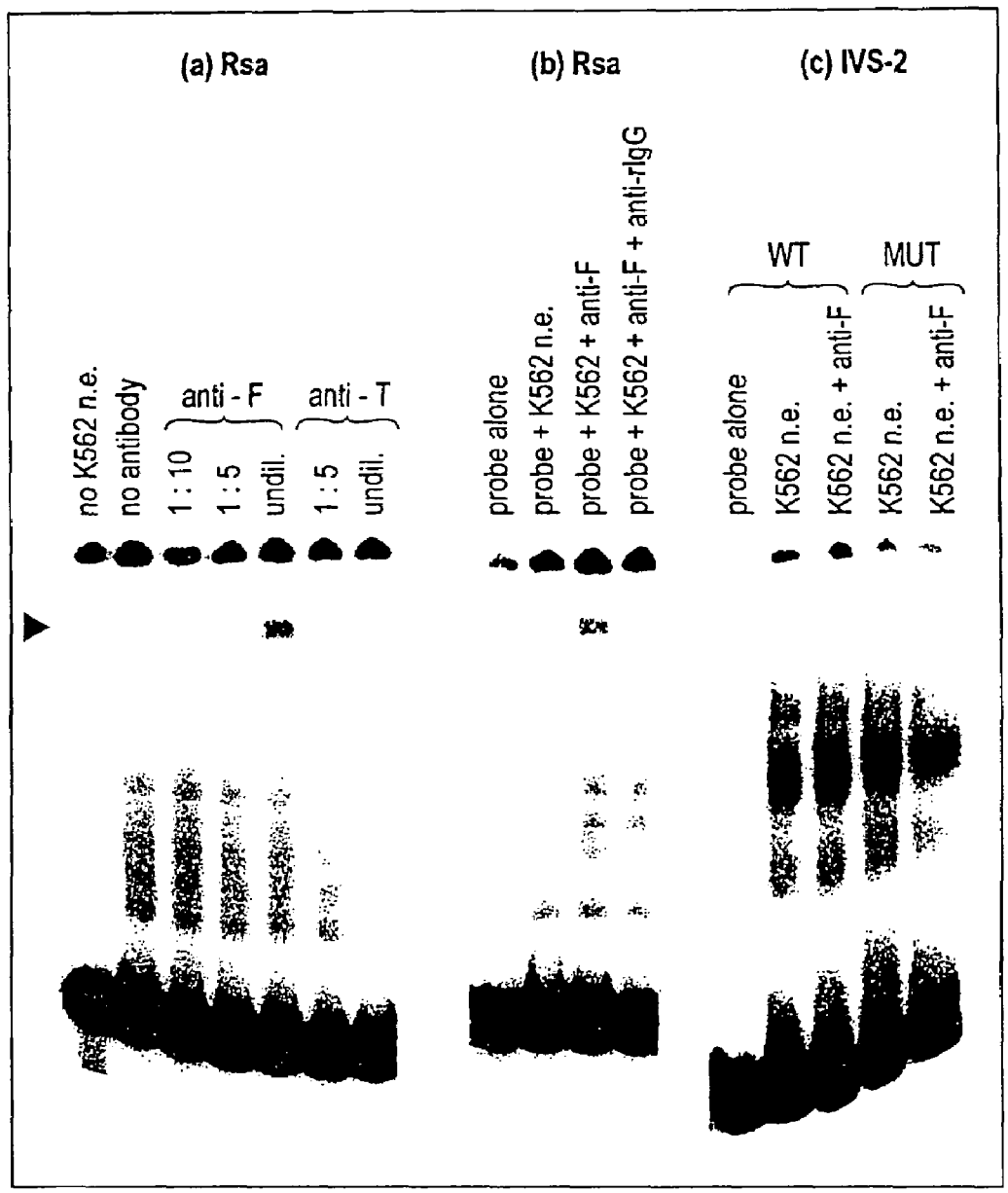
FIG. 2C shows Control experiments showing the specificity of the anti-ferritin supershift assay. Left set of lanes(a): anti-F (anti-ferritin) gives the supershift (arrow); anti-T (anti-transferrin) does not. Center set of lanes (b): anti-F supershift is inhibited by anti-rabbit-IgG. Right set of lanes (c): Using normal or mutant sequences from the 2nd intron (IVS-2) of the human β-globin gene as probes, primary shift bands with K562 nuclear extract were obtained; however, none were recognized by the anti-F (i.e., no supershift bands were obtained).

Enrichment of a ferritin-like protein from K562 cell nuclear extracts. A polyclonal antiserum to human spleen ferritin (which is composed of a mixture of heavy and light chains of ferritin) was found to cause a supershift of part of the DNA-protein complexes formed from crude K562 nuclear extract and the −222/−128 restriction fragment, and the intensity of the super-shift band was proportional to the amount of antiserum added (FIG. 2b). The supershift with anti-ferritin antiserum was found to be specific for this DNA-protein complex, very little-to-no DNA was shifted in the absence of nuclear extract, neither anti-transferrin antiserum nor nonimmune rabbit serum (not shown) shifted the complex, anti-rabbit IgG inhibited the supershift, and protein complexes with other DNAs such as β-IVS2 were not shifted by the anti-ferritin antiserum (FIG. 2C).

Ferritin, unlike most proteins, is resistant to proteinase K digestion and heat at 75° C., and can be obtained ninety percent pure from extracts of embryonic/larval erythroid cells using these two treatments. When this procedure was applied to K562 nuclear extracts, the remaining protein gave a single shift band with the −222/−128 restriction fragment (FIG. 2b, third lane from the left). Furthermore, when the anti-ferritin antiserum was added to the reaction mixture after incubation of the DNA and binding protein, a larger complex was formed, resulting in a supershift band (FIG. 2b, fourth lane). It should be noted that the primary shift band with nuclear extract treated with proteinase K did not shift as far as the gel bands obtained with untreated extract. The inventors have investigated this in a series of timed digests and have found that ferritin is subject to partial digestion by proteinase K; what remains after a 10-15 min digestion (e.g., FIG. 2c, third lane) appears to be a proteinase K-resistant core that still binds DNA. Furthermore, increasing the amount of the enriched peptide preparation gives an increasing intensity to the shift band, and the band gradually moves up the gel as the complex builds in amount.

Figure 3B:
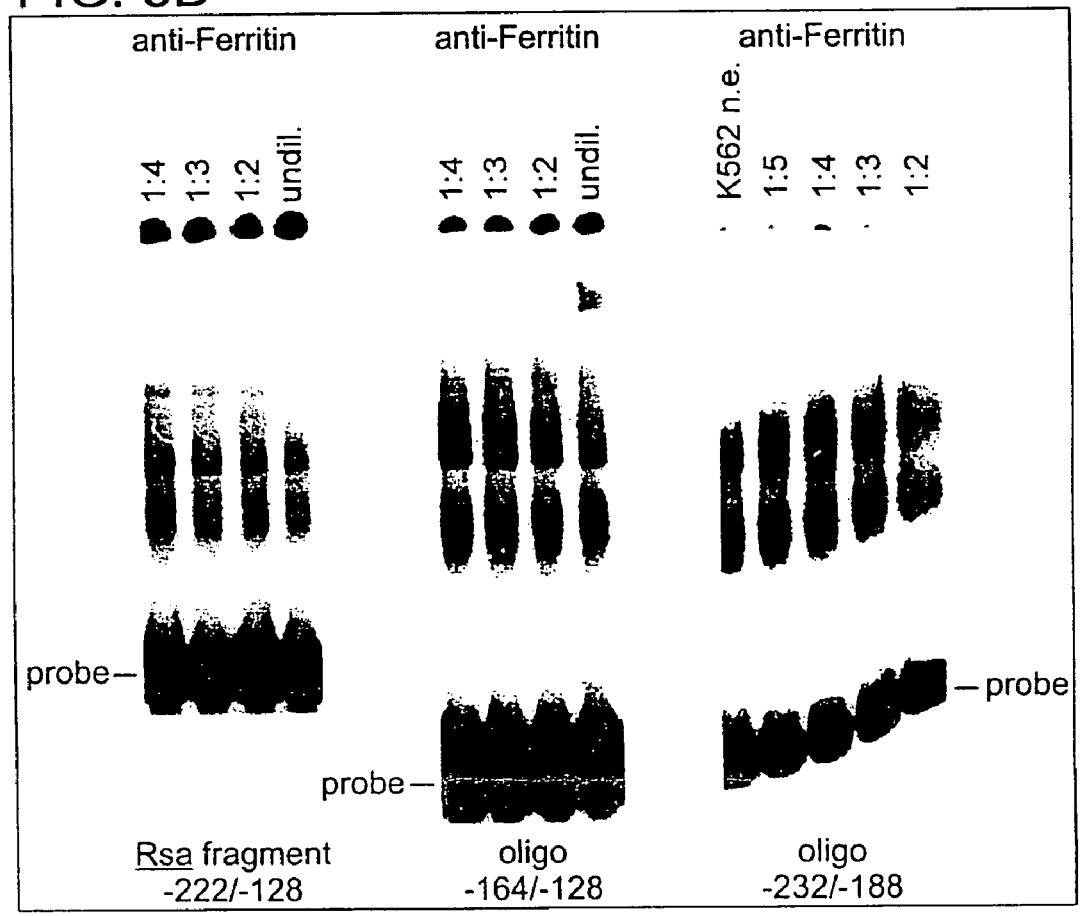

As shown in FIG. 3B, the left series of lanes, a single supershift band was obtained (arrow) with the 95-bp distal promoter that increased in intensity with increasing antiserum. To further localize the binding of the anti-ferritin reactive protein, the supershift was also performed with 32 P-labeled double-stranded oligonucleotides of the −232/−188 and −164/−128 sequences. The more 39 oligonucleotide gave a supershift band, whereas the more 59 oligonucleotide did not (FIG. 3B), indicating that the protein recognized by the antiserum binds to a 37-bp sequence between −164 and −128. The lack of a supershift with the −232/−188 oligonucleotide also serves as a control for the specificity of the antibody.

Localization of the binding region with the antibody supershift assay. The antibody gel shift was also used with $^{32}$P-labeled double stranded oligonucleotides corresponding to the 3' and 5' ends of the 95 bp restriction fragment (FIG. 3A) and with crude K562 nuclear extracts to further localize the binding of ferritin. Thus only the 3' oligo gave the supershift band (FIG. 3B), indicating that the protein recognized by the antiserum binds to a 37 base pair (bp) sequence between −164 and −128.

Figures 4A, 4B:
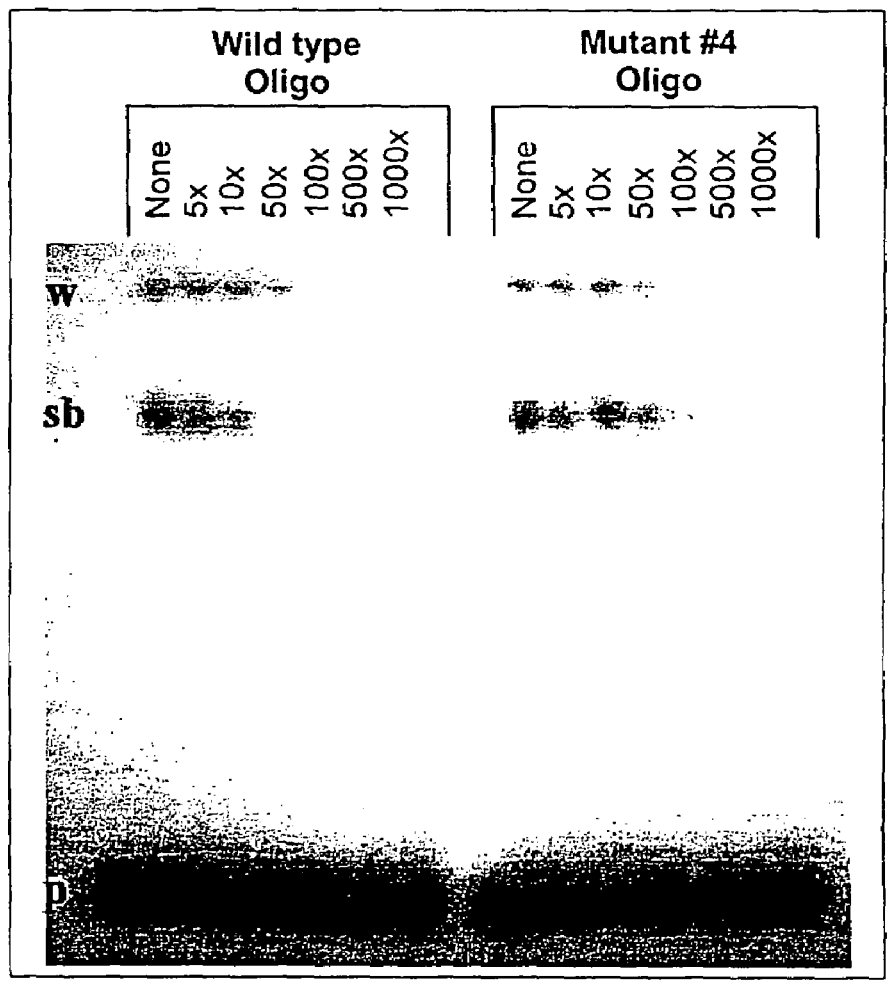
FIG. 4A-4D Definition of the binding site of nuclear ferritin, using oligonucleotide competition assays.
Figures 4C, 4D:
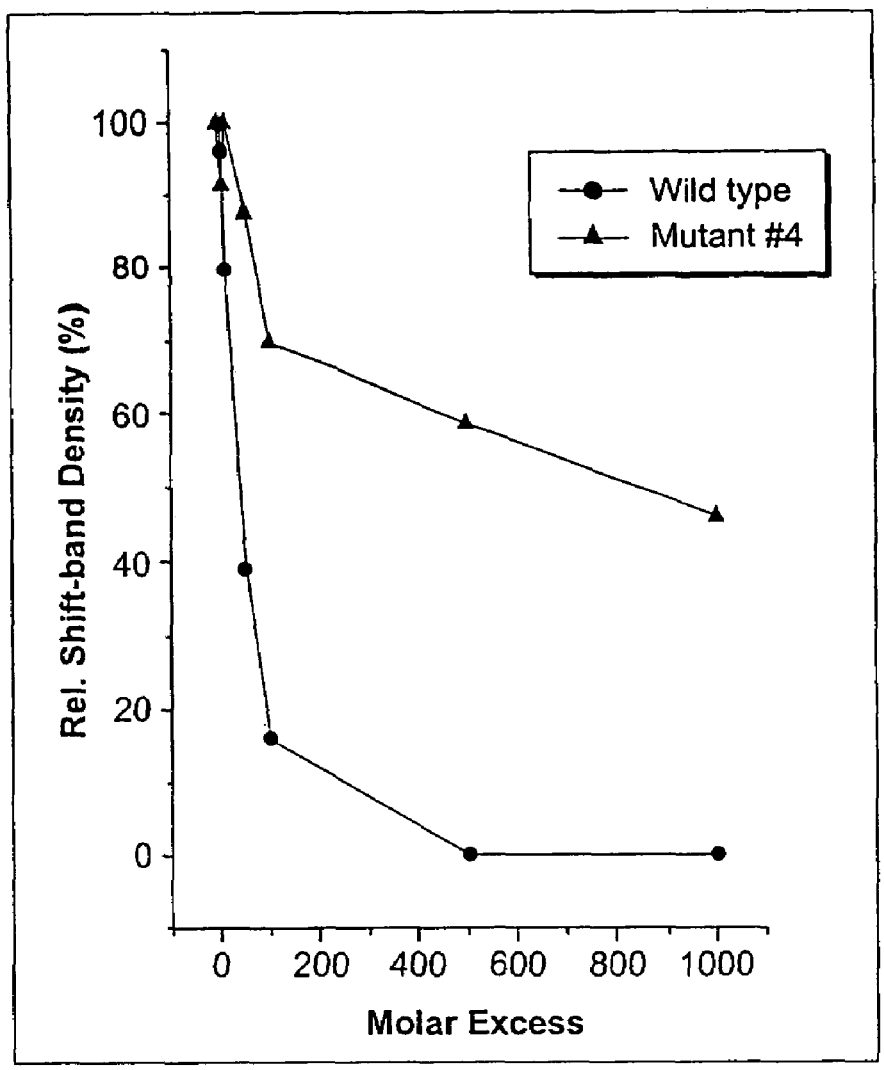

Definition of the binding site with competition gel shifts. To further localize the binding of ferritin, the inventors mutated the 37 bp oligonucleotide in different places, replacing six nucleotides at a time with all A's, all C's, or all G's, with complementary nucleotide replacements in the opposing strand (FIG. 4A). A competition gel shift assay was done with the partially purified protein from heated K562 nuclear extract, in which each of the unlabeled mutant oligos as well as the native sequence was competed against the 32-P-labeled native sequence for binding. All mutants competed for binding as well as the native sequence except those mutated in the −153/−148 region, i.e., mutated in the sequence CAGTGC (e.g., FIG. 4D). The inventors conclude that these six base pairs comprise the binding site of ferritin-H. In FIG. 4C, the specificity of this binding is titrated and quantified in oligo competitions with the unlabeled native sequence compared with the sequence mutated in all of the six nucleotides found to be important for binding, i.e., the sequence CAGTGC (native) compared with mutant #4 (FIG. 4A). Whereas the binding to the labeled native sequence is significantly competed with 50-fold excess of unlabeled self, it took 1,000-fold excess of the unlabeled mutant oligo to begin to compete with the binding to the native sequence, a twenty-fold difference.

Sequence alignments of the promoters (−162/+1) from twelve mammalian adult β-globin genes show that the −150 CAGTGC of the human β-promoter is very highly conserved. In a phylogenetic comparison of twelve mammalian adult β-globin promoters from the cap site to −162 (FIG. 5), the inventors have found that the CAGTGC sequence in the −150 region is among the most conserved of the cis-acting elements, second only to the TATA and CCAAT boxes in its high degree of conservation, as highly conserved as the proximal CACC motif and more highly conserved than the distal CACC.

Discussion

The inventors' results show that in CV-1 cells, an expression clone of human H-ferritin down-regulates expression of an EKLF-stimulated b-globin promoter-driven CAT reporter gene (FIG. 1). The inventors have identified a protein in K562 cell nuclear extracts that has unique properties, i.e., stability to proteinase K and heat (75° C.) and reactivity with anti-ferritin antisera. Ferritin-H binds to a 5' region of the β-globin gene that is required for activation of the β-globin gene in K562 and normal erythroid cells, i.e., the region between −128 and −222 from the cap site (FIG. 3). This DNA region has been shown to bind native human ferritin in gel shift experiments (FIG. 2). The specificity of the binding of the ferritin-like protein has been confirmed using different DNA segments and oligonucleotides in an antibody gel shift assay, and the oligos and antiferritin antiserum have been used to show that the binding site is between −128 and −165 (FIG. 3). Competition gel shift assays with mutated oligonucleotides have shown that the binding of ferritin requires the nucleotides CAGTGC, at −153/−148 of the human β-globin gene; and when this CAGTGC motif is mutated, in vitro binding is reduced approximately twenty fold (FIG. 4). The ability of ferritin-H to repress in this system is abolished, but EKLF-stimulation is retained, when the −153/−148 ferritin binding site is mutated in the co-transfected b-globin-reporter plasmid (FIG. 6). These results show that ferritin H can repress the human adult b-globin gene by binding the promoter in a sequence-specific manner. The biology of ferritin-H and its highly conserved binding site (FIG. 5), as well as its demonstrated function in transient assays, mean that in K562 cells it is indeed functioning as a b-globin repressor. Such a repressor is useful in ameliorating sickle cell and other genetic diseases.

It is noteworthy that an RNA sequence CAGUGN has previously been found to function in the regulation of translation and stability of mRNAs coding for proteins involved in iron metabolism, e.g., mRNAs for ferritin subunits and for the transferrin receptor. In this quite different context, the hexanucleotide is at the apex of a stem-loop structure referred to as an IRE (iron-responsive element), a stable secondary structure formed in the 5' or 3' untranslated regions of the single-stranded mRNAs. The regulatory protein which binds to the IRE (the IRE-BP) has been identified as the cytosolic form of aconitase, a cubane iron-sulfur cluster protein with a molecular mass close to 97 kDa. In contrast, the heat-stable, ferritin-H recognizes the CAGTGC sequence in DNA and apparently has a molecular mass of about 20 kDa, or less if partially proteolyzed.

Globin gene regions are enriched in CAGTGC/CAGTGN sequences relative to the frequency one would expect for the sequence to occur at random. The human genome, as well as the 73,326 bp sequence of the β-like globin gene cluster on chromosome 11, is approximately forty percent G+C. Therefore, the frequency of occurrence of G and C nucleotides will be 0.2 each, and the frequency of A and T will be 0.3 each. The random frequency of occurrence of the sequence CAGTGC will be $(0.2)(0.3)(0.2)(0.3)(0.2)(0.2)=0.000144$. Therefore, the sequence would be expected to occur by chance ten-to-eleven times in the 73,326 bp of the β-like cluster. The actual occurrence is thirty-six times, three-to-four times the number expected by chance. Similarly, the pentamer CAGTG (in the sequence CAGTGN) occurs 205 times, again about four times the fifty-two/fifty-three occurrences expected by chance. The function of this sequence, like other cis-regulatory elements, is context-dependent. The sequence occurs in the 5' and 3' regions of the epsilon- and gamma-globin genes, but these locations and their surrounding sequences are markedly different from the −153 location for the β-globin gene. Binding of Ferritin-H to sites 5' and/or 3' to the epsilon- and gamma-globin genes will have a stimulatory rather than an inhibitory effect on transcription.

Phylogenetic footprinting is useful for identifying important binding sites for regulatory proteins. In this regard, it is interesting that the CAGTGC/CAGTGN sequence is very highly conserved in sequence and location within mammalian β-globin gene promoters (FIG. 5), and is found in the β-promoters of chickens and frogs as well. The high conservation of this sequence means that this binding site has an important function. The Xenopus adult major β-globin gene has the CAGTGC sequence at −45 from the cap site, and an oligonucleotide containing this sequence binds the human ferritin-H from K562 nuclear extracts more strongly than the corresponding region of the human β-globin promoter. Consistent with the inventors' discovery that ferritin-H acts as a repressor of adult β-globin in human K562 cells is the inventors' finding that the −150 binding site for this protein competes with the mouse β-major −160 site known to bind the repressor protein BB1.

EXAMPLE 2

Materials and Methods

Materials: Calf intestine alkaline phosphatase, T4 polynucleotide kinase, and Sau 96 I were obtained from Promega/Fisher. 32P-γ-ATP was from Dupont/NEN. Polyclonal (rabbit) antiserum to human spleen ferritin was obtained from Sigma Chemical Company. All other reagents were molecular biology grade.

Restriction fragments and oligonucleotides: The 5' region of the human beta globin gene (from −610 to +20), previously cloned in pSVOCAT, was cut from the purified plasmid by digestions with Hind III and Bam HI. The 630 bp fragment was phenol/chloroform treated, dephosphorylated, and end-labelled with 32-P. Synthetic oligonucleotides corresponding to the core/BP-1 binding site of NCR1 (−584/−527), the more distal of the two 5'-β-globin silencers, and −164/−128 region of the promoter were purified and annealed, and the double-stranded oligos were end-labeled as above and/or used as unlabeled competitors in gel mobility shift assays.

Preparation of nuclear extracts: Nonadherent K562 cells were grown in suspension in a medium composed of RPMI 1640 and 15% fetal bovine serum as described and harvested at a density of 106 cells per ml. For each preparation, nuclear extract was prepared from two liters of cells. Protein content of the extracts ranged from 3 to 6 mg/ml. Extracts enriched approximately 80% in proteins which specifically bind the −150 promoter region and the −550 silencer region were prepared by treating the crude extracts with heat at 80° C.

Gel mobility shift assays: Gel retardation assays (i.e., gel shifts) were used to determine DNA binding of the partially purified extract proteins, first to the synthetic oligonucleotides corresponding to −550 silencer and to the −150 region of the promoter, and subsequently to the 630 bp fragment of the human β-globin gene containing both the promoter and upstream regulatory sequences with the modifications described in the legend to FIG. 11. Gels used for retardation assays were 4% acrylamide and the running buffer was low ionic strength TAE.

Experimental design: The DNA looping assay is performed by mixing an extract containing proteins specific for regulatory sites that are proposed to interact, with DNA containing the contiguous sites separated by intervening DNA; and the binding of the proteins is detected with a standard EMSA. If proteins bound to separate sites interact with each other in a stable way, the intervening DNA will form a loop which can be cut at a unique restriction site in the loop. The test for looping is that the DNA-protein complex retains its EMSA migration as a single band after the cut. Controls include lanes with deproteinized aliquots of the reaction before and after the restriction digest, to prove that the loop was indeed cut. The conditions used for cutting the looped complex with Sau 96 I are given in the legend to FIG. 11.

Results

We have reported in a preliminary paper that a restriction fragment containing part of the distal promoter of the human β-globin gene, from −222/−128 bp, is bound by ferritin-H protein in K562 cell nuclear extracts, and is specific for the −150 region. At least two proteins specific for the functionally defined silencers that map upstream of the proximal and distal promoter of the human β globin gene, in the regions of −300 (−338/−233) and −530 (−610/−490) from the cap site. With the ultimate aim of exploring interactions between these silencers and the β-promoter, we designed an experimental approach for detecting DNA looping stabilized by interactions between proteins bound to sites separated by moderate lengths of intervening DNA. We have used a partially purified K562 cell nuclear extract that contains proteins that bind these separate regions.

Figure 8:
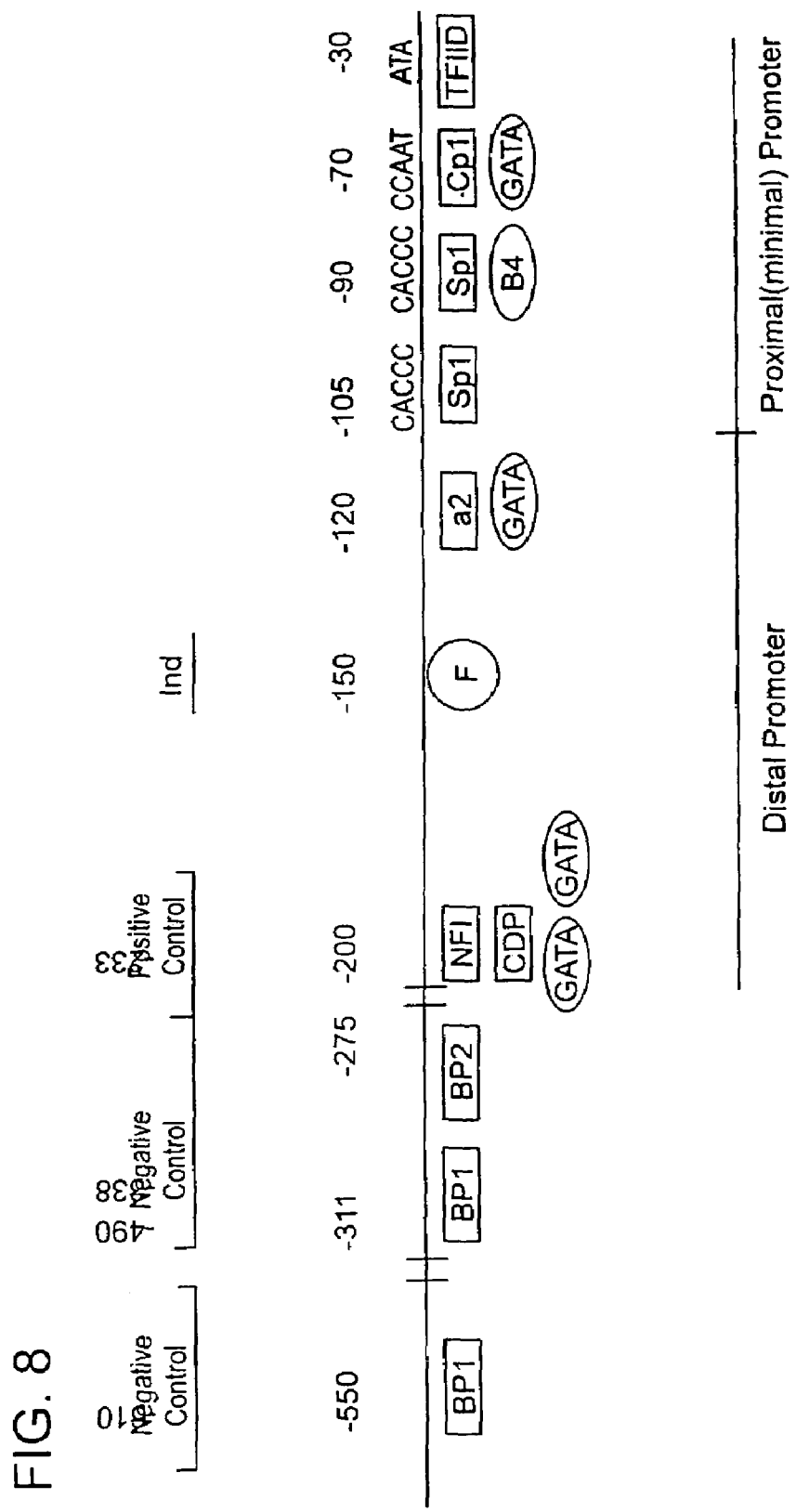
FIG. 8 shows the protein-binding sites 5' to the human beta globin gene. General factors are shown in rectangles, erythroid-specific factors are shown in elipses, and the ferritin protein is shown as a circle.
Figure 9:
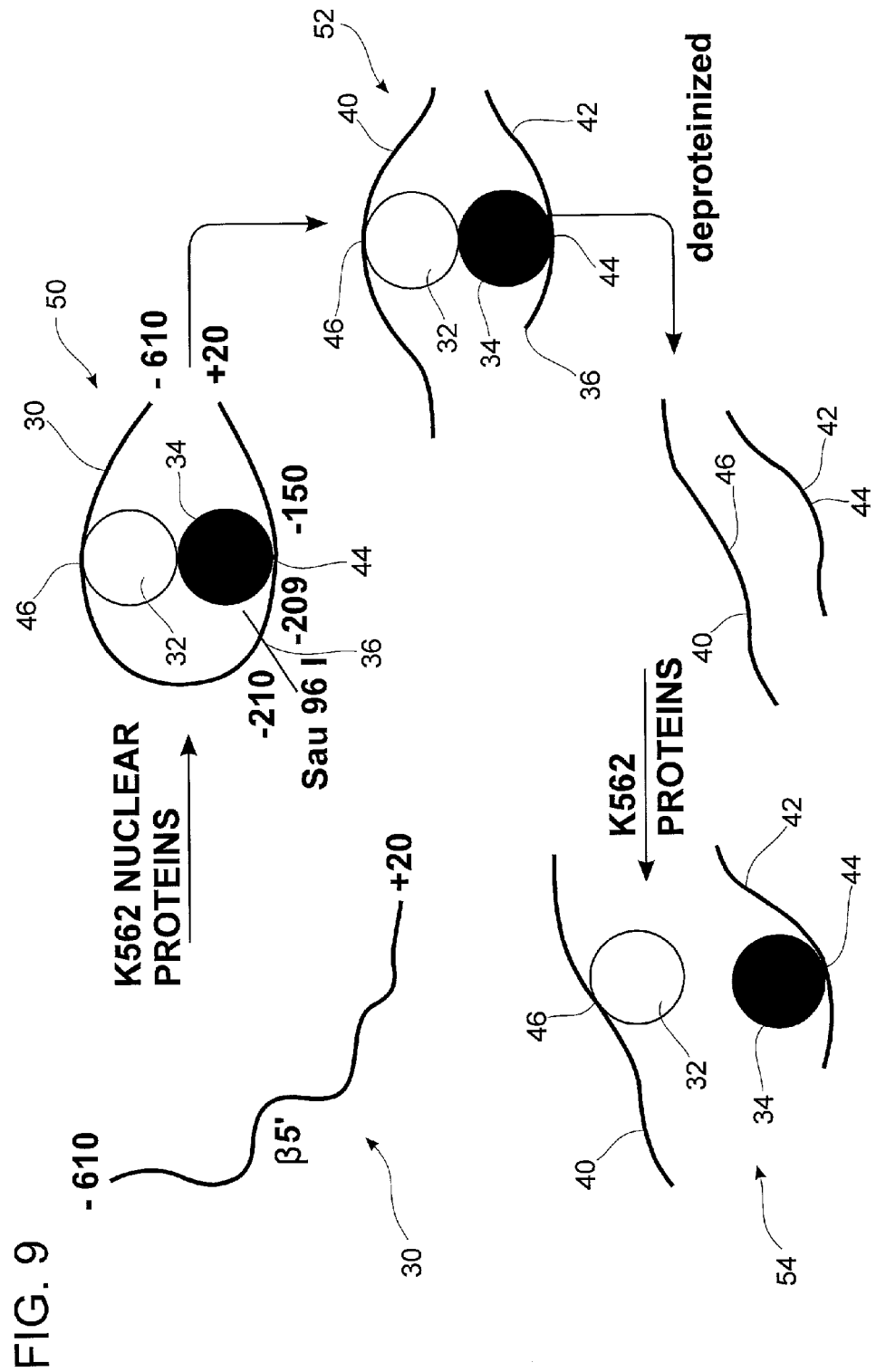
FIG. 9 shows a diagrammatic interpretation of the DNA looping experiment in example 2. 5' promoter region 30 corresponds to lanes 1 and 4 in FIG. 10, protein/DNA complex 50 to lane 2 (before cutting with Sau 96I), protein/DNA complex 52 to lane 3 (after cutting), deproteinized fragments 40 and 42 to lanes 5 and 6, and protein/DNA mixture 54 to lane 7. In this explanation, a protein or proteins bound to the promoter, drawn as a dark circle (e.g., the protein bound at the −150 site) interacts with a protein or proteins (drawn as an open circle) bound upstream of the −210 restriction site (e.g., one or both of the two previously described silencer-binding proteins), resulting in a looping of the intervening DNA which can be cut with the restriction enzyme without disturbing the complex or its mobility as a single band in the gel shift assay.
Figure 10:
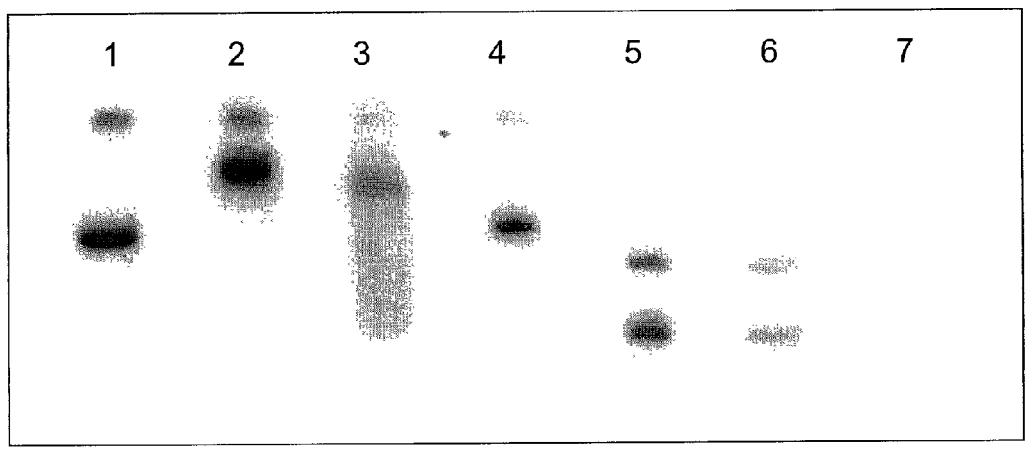
FIG. 10 DNA looping in vitro with the −610/+20 β-globin DNA and partially purified proteins from K562 nuclear extracts.

FIG. 8 is a diagram of the β-globin gene 5' region used as a probe in these experiments. FIGS. 11 and 10 show EMSAs using this 630 bp probe (−610/+20) combined with restriction digests to demonstrate looping, and FIG. 9 gives a diagrammatic interpretation of the results. The partially purified protein extract used for these experiments was found to contain both the −150 promoter-binding protein and silencer(−530)-binding activity by separate gel shift assays with their respective oligonucleotides (data not shown).

FIG. 10, lane 1, and FIG. 11, lane 1, show the migration of the DNA alone, which gives a single band. In lane 2 of FIGS. 10 and 11, all of the DNA is retarded in its migration, due to the binding of proteins from the partially purified K562 nuclear extract. In lane 3 of FIGS. 10 and 11, the material was reacted with the restriction enzyme Sau 96 I, after the DNA and proteins had formed a complex; the large majority of this material was retarded in its migration similar to that in lane 2. (As shown in FIG. 8, there is a single Sau 96 I site in the 5' β-globin sequence, at −210, which cuts the DNA between the promoter and the upstream regions.) In lanes 4 and 5 of FIGS. 10 and 11, the complexes in lanes 2 and 3, respectively, were deproteinized and run as the pure DNA, showing that one large piece of DNA was recovered from the complex in lane 2, whereas all the DNA from the complex in lane 3 was cut, giving two clean bands (lanes 5) identical in their migration to bands obtained when pure DNA was reacted with the restriction enzyme (lane 6, FIG. 10). The lengths of these fragments are 229 bp (+20/−209, containing the promoter) and 401 bp (containing the upstream sequences, including the silencers). When the mixture containing these fragments of pre-cut DNA was reacted with the partially purified proteins, the two fragments were shifted independently, but the large (looped) complex was not formed (lane 7, FIG. 10). The observed fact that the complex detected in lane 2 of both figures holds together after the DNA has been cut completely with Sau 96 I indicates that a loop was initially formed between a site or sites downstream from −209 and a site or sites upstream from −210.

An interpretive drawing of these results is shown in FIG. 9, and the legend indicates which parts of the drawing correspond to which gel lanes in FIG. 10. FIG. 9 shows a schematic diagram of the β-globin gene 5' region 30 and the experiments used to elucidate protein binding to it. Ferritin 34 binds to promoter region 30 at ferritin binding site 44. Several DNA binding proteins 50 also bind to the β-globin promoter region. Binding proteins 50 all bind upstream of the ferritin binding site 44. Repression of the β-globin gene by ferritin is enhanced by a protein-protein interaction between ferritin and at least one of the promoter binding proteins 50. FIG. 9 illustrates the protein-protein-DNA complex ferritin 34 forms with at least one of binding proteins 32. Promoter region 30 has a ferritin binding site 44 and upstream of that a protein binding site 46. Binding protein 32 attaches to binding site 46, and ferritin 34 binds to ferritin binding site 44. Ferritin 34 and binding protein 32 then bind to one another, thereby creating a loop in the DNA. Promoter region 30 may be cut into two smaller fragments 40 and 42 at restriction enzyme site 36 by restriction enzyme Sau96I. Because of the protein-protein interaction between binding protein 32 and ferritin 34, the complex remains intact. Thus, application of a restriction enzyme does not result in a mobility shift on a gel assay. This can be seen in lanes 2 and 3 of both FIG. 10 and FIG. 11. Removing proteins from the uncut DNA loop results in an intact promoter region 30 illustrated in lane 4 of FIG. 10 and land 4 of FIG. 11. Removing proteins from the DNA loop after being cut by a restriction enzyme results in two DNA fragments 40 and 42. These fragments may be seen in lane 5 of FIG. 10 and lane 5 of FIG. 11. Lane 7 of FIG. 10 shows the result of adding nuclear extract to fragments 40 and 42. The same complex found in lane 3 may be formed by adding nuclear extract to DNA fragments 40 and 42.

When promoter fragments 40 and 42 are combined with a nuclear extract having ferritin 34 and binding protein 32, a gel shift results. This is shown in lane 7 of FIG. 10. This shows that the DNA loop is caused by ferritin binding to the promoter region.

Controls: Controls incorporated into the experiments described above, as depicted in FIGS. 10 and 11, include deproteinizing the complexes to show that the loop was cut by the restriction enzyme, and showing that unrelated DNA sequences (e.g., P. putida DNA) do not form a complex with this extract. As a further control, the single-band complex in lane 3 from gels identical to that in FIG. 11 was isolated, deproteinized, and also shown to contain equal amounts of the two restriction fragments resulting from Sau 96 I digestion. As shown in FIG. 10, lanes 6 and 7, the two Sau 96 I fragments of the beta globin 5' region shift independently with this extract and do not form the large complex unless they are linked; furthermore, an approximately eight-fold greater protein concentration is required to begin to shift the separated restriction fragments than is required to initiate formation of the looped complex.

Discussion

Interpretations: The reported experiments have shown that DNA looping can be detected in vitro with an EMSA assay combined with digestion with a specific restriction enzyme. in these DNA looping experiments, the results show that sequences between −209 and +20 bp of the human β-globin gene interact with upstream sequences between −210 and −610 bp. The looping is mediated by a partially purified extract containing a −150 promoter-binding protein and β-globin silencer-binding protein, confirmed by binding experiments with the extract and the separate binding sequences. When the single, large DNA-protein complex detected by our EMSAs was cut with Sau 96 I, the complex still migrated as a single, large complex high on the gels. (There was a small increase in migration of the cut complex which is to be expected since a single, double-stranded restriction cut will change the DNA conformation slightly.) It should also be noted that the binding of the proteins in this looped complex appears to be very tight; it takes a high excess of unlabeled −164/−128 and −584/−527 oligonucleotides to break up the complex (not shown). Furthermore, a comparison of the binding affinity of the full 630 bp DNA with the binding affinities of a mixture of the fragments generated by Sau 96 I, showed that it takes approximately eight-fold less protein to form a shifted complex with the large, intact (630 bp) DNA than with a mixture of the separate fragments, showing that the binding to the larger 630 bp DNA is cooperative and that looping is occurring.

All of these results are consistent with known parameters and forces controlling DNA looping, which is mediated by two or more proteins showing cooperative (and, usually, tight) binding. The results of these experiments also show that repression of the β-globin gene by upstream silencers can be mediated by DNA looping. This approach does not allow one to determine the identity of the proteins involved and may not work in cases where there is DNA supercoiling, as with certain plasmid contructs in vitro, or weak protein-protein interaction.

The loop in the promoter region formed by the interaction between ferritin and one or more upstream binding proteins enhances repression of the β-globin gene. Human cells generally have sufficient amounts of upstream binding proteins such that addition of ferritin alone to a human cell by the methods described herein is generally sufficient to cause repression of the β-globin gene and other genes regulated by this activity. In addition, binding of ferritin to the CAGTGC ferritin binding site is generally sufficient to repress transcription of the β-globin gene.

One method of increasing ferritin-H expression is to repress expression of ferritin-L or other ferritin family proteins. This may be accomplished by using antisense DNA oligonucleotides specific for the genes that encode ferritin family proteins other than ferritin-H. Reduction and expression of these ferritin proteins leads to a higher concentration and heightened expression of ferritin-H. By shifting the ratios between ferritin-H and other ferritin family proteins, β-globin is repressed and the deleterious effects of sickle cell anemia are reduced to acceptable levels.

Heightened expression of ferritin-H also cures intracellular iron mismanagement, resulting in lower levels of harmful ferrous ions. While ferritin-H ferroxidase activity may play a role in proper management of intracellular iron, higher concentrations of ferritin-H affect expression of a number of genes involved in iron metabolism. This genetic regulatory function of ferritin-H facilitates proper iron management in cells that have been adversely affected by a wide variety of diseases. As described in the background, cancer, neurodegenerative diseases, neuromuscular disorders and atherosclerosis all lead to improper iron management within the body's cells. Increasing the concentration of ferritin-H and the resulting genetic regulatory effects alleviate the deleterious effects of improper iron management.

Studies have shown that ferritin-H exhibits the most efficient ferroxidase activity when it is expressed at roughly the same levels as ferritin-L. Equal expression levels result in the highest number of ferritin-H/ferritin-L heteropolymers. The heteropolymeric form of the 24-mer ferritin complex is the most efficient at converting the ferrous ion to the ferric ion and at sequestering iron ions. This suggests that maintaining equal concentrations of ferritin-H and ferritin-L is most likely to result in proper iron management. Increasing levels of ferritin-H would result in the formation of ferritin-H homopolymers. Ferritin-H homopolymers exhibit low ferroxidase activity. It would be expected that this would lead to higher levels of the more harmful ferrous ion and have adverse affects on the cells. However, the inventors have discovered that the gene regulatory functions of ferritin-H causes just the opposite to occur.

Those skilled in the art will realize that there are a number of ways in which to elevate levels of ferritin-H within a cell. It may involve introduction of the ferritin-H protein itself by any number of pharmaceutically acceptable means well known to those skilled in the art. This may include using liposomal constructs containing Ferritin-H protein. These constructs may or may not have ligands or antibodies.

An alternative method for increasing intracellular levels of ferritin-H is to regulate expression of ferritin family molecules. This may be done in a number of ways. Antisense DNA oligonucleotides that target ferritin family genes other than ferritin-H will result in decreased expression of the targeted gene and cause greater concentrations of ferritin-H within the cell. It is also possible to introduce proteins or other compounds that increase transcription or translation of an endogenous ferritin-H gene or a related Ferritin family gene. These activating compounds may be introduced to cells in methods similar to the introduction of the ferritin-H protein itself as discussed above.

Yet another method of increasing intracellular levels of ferritin-H is to introduce a ferritin-H expressing vector into the cells. Those skilled in the art will appreciate that there are a number of methods to transfect cells with a number of different vectors, including plasmids, phagemids, and cosmids. The type of vector used, the promoter region within the vector and any control sequences used with the vector will vary depending on a variety of factors known to those skilled in the art. These factors include but are not limited to the cell tissue targeted, the level of desired expression and the level of ferritin family protein expression within the targeted cells.

Yet another method of increasing intracellular levels of ferritin-H is to increase levels of proteins or compounds that elevate transcription or translation of ferritin-H promoters.

Methods of increasing intracellular methods may be considered either intracellular induction methods, where the cell creates its own ferritin, or extracellular introduction methods, where Ferritin is added to the cell as when liposomal constructs are used.

Transfection of cells with vectors coding for a ferritin family protein may be performed either ex vivo or in vivo. When performed in vivo, the vectors are introduced into the patient's body. When performed ex vivo, cells are transfected with a vector and then implanted into the patient's body tissue. Stem cells are especially well suited for this, however other cells may also be used.

Whereas, the present invention has been described in relation to the drawings attached hereto, it should be understood that other and further modifications, apart from those shown or suggested herein, may be made within the spirit and scope of this invention.

Citations in the following list of References are incorporated in pertinent part by reference.

REFERENCES

1. Blau, C. A. & Stamatoyannopoulos, G. (1994) *Curr Opin Hematol* 1, 136-42.
2. Orkin, S. H. 1995) *Eur J Biochem* 231, 271-81.
3. Bieker, J. J. (1998) *Curr Opin Hematol* 5, 145-50.
4. Dover, G. J. & Boyer, S. H. (1987) *Blood* 69, 1109-13.
5. Rodgers, G. P., Dover, G. J., Noguchi, C. T., Schechter, A. N. & Nienhuis, A. W. (1989) *Prog Clin Biol Res,* 281-93.
6. Andrews, N. C., Erdjument-Bromage, H., Davidson, M. B., Tempst, P. & Orkin, S. H. (1993) *Nature* 362, 722-8.
7. Jane, S. M., Gumucio, D. L., Ney, P. A., Cunningham, J. M. & Nienhuis, A. W. (1993) *Mol Cell Biol* 13, 3272-81.
8. Tsai, S. F., Martin, D. I., Zon, L. I., D'Andrea, A. D., Wong, G. G. & Orkin, S. H. (1989) *Nature* 339, 446-51.
9. Armstrong, J. A., Bieker, J. J. & Emerson, B. M. (1998) *Cell* 95, 93-104.
10. Bieker, J. J., Ouyang, L. & Chen, X. (1998) *Ann N Y Acad Sci* 850, 64-9.
11. Li, Q., Clegg, C., Peterson, K., Shaw, S., Raich, N. & Stamatoyannopoulos, G. (1997) *Proc Natl Acad Sci USA* 94, 2444-8.
12. Donze, D., Townes, T. M. & Bieker, J. J. (1995) *J Biol Chem* 270, 1955-9.
13. Fordis, C. M., Nelson, N., Dean, A., Schechter, A. N., Anagnou, N. P., Nienhuis, A. W., McCormick, M., Padmanabhan, R. & Howard, B. H. (1985) *Prog Clin Biol Res* 191, 281-92.
14. Fordis, C. M., Nelson, N., McCormick, M., Padmanabhan, R., Howard, B. & Schechter, A. N. (1986) *Biochem Biophys Res Commun* 134, 128-33.
15. Dean, A., Ley, T. J., Humphries, R. K., Fordis, C. M., Jr. & Schechter, A. N. (1983) *Prog Clin Biol Res* 134, 323-34.
16. Dean, A., Ley, T. J., Humphries, R. K., Fordis, M. & Schechter, A. N. (1983) *Proc Natl Acad Sci USA* 80, 5515-9.
17. Theil, E. C. (1987) *Ann Rev Biochem* 56, 289-315.
18. Dickey, L. F., Sreedharan, S., Theil, E. C., Didsbury, J. R., Wang, Y. H., & Kaufman, R. C. (1987) *J Biol Chem* 262, 7901-7907.
19. Wu, Y. J. & Noguchi, C. T. (1991) *J Biol Chem* 266, 17566-72.
20. Arosio, P., Yokota, M., & Drysdale, J. W. (1976) *Cancer Res* 36, 1735-1739.
21. Harrison, P. M., & Arosio, P. (1996) *Biochim Biophys Acta* 1275, 161-203.
22. Ferreira, C., Bucchini, D., Martin, M. E., Levi, S., Arosio, P., Grandchamp, B., & Beaumont, C. (2000) *J Biol Chem* 275, 3021-3024.
23. Broyles, R. H., Blair, F. C., Kyker, K. D., Kurien, B. T., Stewart, D. R., Hala'sz, H., Berg, P. E., & Schechter, A. N. (1995) *Colloque INSERM* 234, 43-51.
24. Picard, V., Renaudie, F., Porcher, C., Hentze, M. W., Grandchamp, B. & Beaumont, C. (1996) *Blood* 87, 2057-64.
25. Cai, C. X., Birk, D. E. & Linsenmayer, T. F. (1998) *Mol Biol Cell* 9, 1037-51.
26. Cai, C. X., Birk, D. E. & Linsenmayer, T. F. (1997) *J Biol Chem* 272, 12831-9.
27. Pountney, D., Trugnan, G., Bourgeois, M. & Beaumont, C. (1999) *J Cell Sci* 112, 825-31.
28. Cheepsunthorn, P., Palmer, C. & Connor, J. R. (1998) *J Comp Neurol* 400, 73-86.
29. deBoer, E., Antoniou, M., Mignotte, V., Wall, L. & Grosveld, F. (1988) *Embo J* 7, 4203-4212.
30. Macleod, K. & Plumb, M. (1991) *Mol Cell Biol* 11, 4324-32.
31. Berg, P. E., Williams, D. M., Qian, R. L., Cohen, R. B., Cao, S. X., Mittelman, M. & Schechter, A. N. (1989) *Nucleic Acids Res* 17, 8833-52.
32. Miller, I. J. & Bieker, J. J. (1993) *Mol Cell Biol* 13, 2776-86.
33. Maniatis, T., Fritsch, E. F. & Sambrook, J. (1989) *Molecular Cloning: A Laboratory Manual* (Cold Spring Harbor Laboratory, Cold Spring Harbor, N.Y.).
34. Kurien, B. T., Scofield, R. H., & Broyles, R. H. (1997) *Anal Biochem* 245, 123-126.
35. Dignam, J. D., Lebovitz, R. M. & Roeder, R. G. (1983) *Nucleic Acids Res* 11, 1475-89.
36. Atkinson, B. G., Dean, R. L., Tomlinson, J. & Blaker, T. W. (1989) *Biochem Cell Biol* 67, 52-7.
37. Fried, M. & Crothers, D. M. (1981) *Nucleic Acids Res* 9, 6505-25.
38. Aziz, N. & Munro, H. N. (1987) *Proc Natl Acad Sci USA* 84, 8478-82.
39. Casey, J. L., Hentze, M. W., Koeller, D. M., Caughman, S. W., Rouault, T. A., Klausner, R. D. & Harford, J. B. (1988) *Science* 240, 924-8.
40. Hentze, M. W., Caughman, S. W., Rouault, T. A., Barriocanal, J. G., Dancis, A., Harford, J. B. & Klausner, R. D. (1987) *Science* 238, 1570-3.
41. Haile, D. J., Rouault, T. A., Harford, J. B., Kennedy, M. C., Blondin, G. A., Beinert, H. & Klausner, R. D. (1992) *Proc Natl Acad Sci USA* 89, 11735-9.
42. Kennedy, M. C., Mende-Mueller, L., Blondin, G. A. & Beinert, H. (1992) *Proc Natl Acad Sci USA* 89, 11730-4.
43. Gumucio, D. L., Shelton, D. A., Bailey, W. J., Slightom, J. L. & Goodman, M. (1993) *Proc Natl Acad Sci U S A* 90, 6018-22.

44. Shterman, N., Kupfer, B. & Moroz, C. (1989) *Cancer Res* 49, 5033-6.
45. Thomson, A. J. (1991) *FEBS Lett* 285, 230-6.
46. Hentze, M. W., Keim, S., Papadopoulos, P., O'Brien, S., Modi, W., Drysdale, J., Leonard, W. J., Harford, J. B. & Klausner, R. D. (1986) *Proc Natl Acad Sci USA* 83, 7226-30.
47. Chang, C. Y., Wu, D. A., Mohandas, T. K. & Chung, B. C. (1990) *DNA Cell Biol* 9, 205-212.
48. Papayannopoulou, T., Brice, M. & Stamatoyannopoulos, G. (1986) *Cell* 46, 469-76.
49. Gribnau, J., Diderich, K., Pruzina, S., Calzolari, R. & Fraser, P. (2000) *Mol Cell* 5, 377-86.
50. Epner, E., Reik, A., Cimbora, D., Telling, A., Bender, M. A., Fiering, S., Enver, T., Martin, D. I., Kennedy, M., Keller, G. & Groudine, M. (1998) *Mol Cell* 2, 447-55.
51. Higgs, D. R. (1998) *Cell* 95, 299-302.
52. Reik, A., Telling, A., Zitnik, G., Cimbora, D., Epner, E. & Groudine, M. (1998) *Mol Cell Biol* 18, 5992-6000.
53. Matsumoto, M. & Komori, N. (2000) in *Enzy.* (Academic Press, New York), Vol. 316 (Chap. 33), pp. 492-511.
54. Gribnau, J., Diderich, K., Pruzina, S., Calzolari, R. & Fraser, P. (2000) *Mol Cell* 5, 377-86.
55. Epner, E., Reik, A., Cimbora, D., Telling, A., Bender, M. A., Fiering, S., Enver, T., Martin, D. I., Kennedy, M., Keller, G. & Groudine, M. (1998) *Mol Cell* 2, 447-55.
56. Higgs, D. R. (1998) *Cell* 95, 299-302; Reik, A., Telling, A., Zitnik, G., Cimbora, D., Epner, E. & Groudine, M. (1998) *Mol Cell Biol* 18, 5992-6000).
57. Broyles et al., "A Ferritin-Like Protein Binds to a Highly Conserved CAGTGC Sequence in the β-globin promoter, In *Sickle Cell Disease and Thalassaemias: New Trends in Therapy* (Y. Beuzard, B. lubin & J. rosa, eds.) colloque INSERM 234:45-51, 1995.
58. Picard et al., "Overexpression of the Ferritin H subunit in cultured erythroid cells changes the intracellular iron distribution," *Blood,* 87:2057-2064, 1996.
59. Cai et al., "Ferritin is a Developmentally Regulated Nuclear Protein of Avian Corneal Epithelial Cells," *J Biol. Chem.,* 272:12831-12839, 1997.
60. Cai et al., "Nuclear Ferritin Protects DNA from UV damage in Corneal Epithelial Cells," *Molec. Biol. Cell,* 9:1037-1051, 1998.
61. Cheepsunthorn et al., "Cellular Distribution of Ferritin Subunits in Postnatal Rat Brain," *J. Comp Neurol.,* 400:73-86, 1998.
62. Poutney et al., "The Identification of Ferritin in the Nucleus of K562 cells, and investigation of a possible Role in the Transcriptional Regulation of adult β-globin gene," *J. Cell Sci.,* 112:825-831, 1999.
63. Dover et al., "Fetal-Hemoglobin Containing Cells Have the Same Mean Corpuscular hemoglobin as Cells Without Fetal Hemoglobin: A Reciprocal Relationship Between Gamma- and Beta-Globin Gene Expression in Normal Subjects and in Those With High Fetal Hemoglobin Production," *Blood,* 69:1109-1113, 1987.
64. Rogers et al., "Hematologic Responses of Patients With Sickle Cell Disease to Treatment With Hydroxyurea," *New Eng. J. Med.,* 322:1037-1045, 1990.
65. Ammendola et al., "Sp1 DNA Binding Efficiency is Highly Reduced in Nuclear Extracts from Aged Rat Tissues," *J. Biol. Chem.,* 267:17944-17948, 1992.
66. Griffiths et al., "Iron in the Basal Ganglia in Parkinson's Disease. An In Vitro Study Using Extended X-ray Absorption Fine Structure and Cryo-electron Microscopy. *Brain,* 122:667-673, 1999.
67. Kirkali et al., "Serum Ferritin as a clinical Marker for Renal Cell Carcinoma: Influence of Tumor Size and volume," *Urol. Int.,* 62:21-25, 1999.
68. Bartzokis et al., "Increased Basal Ganglia iron Levels in Huntington Disease," *Arch. Neurol.,* 56:569-574.
69. Mandishona et al., "Dietary Iron Overload as a Risk Factor for Hepatocellular Carcinoma in Black Africans," *Hepatology,* 27:1563-1566, 1998.
70. Applegate et al., "Evidence That Ferrin is UV Inducible in Human Skin: part of a putative Defense Mechanism," *J. Invest. Dermatol.,* 111:159-163, 1998.
71. Lin et al., "Hemin-enhanced Resistance of Human Leukemia Cells to Oxidative Killing: antisense Determination of Ferritin Involvement," *Arch. Biochem. Biophys.,* 352: 51-58.
72. Broyles R H (1999). Sem. Cell Devel. Biol. 10:259-265.
73. Barker-Harrel J, McBride K A, Broyles R H (1988). Exp.Cell Res. 178:435-448.
74. Bodine D. (2000). Molecular Therapy 2:101-102.
75. Somiari S, Glasspool-Malone J, Drabick J J, Gilbert R A, Heller R, Jaroszeski M J, Malone R W (2000) Molecular Therapy 2:178-187.
76. Hengge U R, Mirmohammadsadegh A. (2000). Molecular Therapy 2:188-194.
77. Lohr F et al. (2000). Molecular Therapy 2:195-203.
78. Bettan M et al. (2000). Molecular Therapy 2:204-210.
79. Bristol J A et al. (2000). Molecular Therapy 2:223-232.
80. Gao G, Sands, M S, Haskins M E, Ponder K P (2000). Molecular Therapy 2:233-244.
81. Chen S J, Rader D J, Tazelaar J, Kawashiri -a, Gao G-p, Wilson J M (2000). Molecular Therapy 2:256-261.
82. Sheridan P L et al. (2000). Molecular Therapy 2:262-275.
83. Abruzzese R V et al. (2000). Molecular Therapy 2:276-287.
84. Wu L, Barry M A (2000). Molecular Therapy 2:288-298.

What is claimed is:

1. A method for repressing production of beta-globin proteins and increasing production of gamma-globin proteins in a human cell, the method comprising:
   providing at least one human beta-globin producing cell;
   providing a vector encoding ferritin-H; and
   inserting, in vitro, the vector encoding ferritin-H into the at least one beta-globin producing cell, whereby ferritin-H is produced in the cell, and the ferritin-H produced represses production of beta-globin proteins in the cell, and activates production of gamma-globin proteins in the cell.

2. The method of claim 1 wherein the step of inserting the vector encoding ferritin-H into the at least one beta-globin producing cell comprises transfecting the at least one beta-globin producing cell with the vector encoding ferritin-H.

3. The method of claim 1 wherein, in the step of providing a vector encoding ferritin-H, the ferritin-H is human ferritin-H.

4. The method of claim 1 wherein the ferritin-H produced binds to at least one of the 5' and 3' regions of the gamma-globin gene of the human beta-globin producing cell and stimulates transcription thereof.

5. The method of claim 1, wherein the ferritin-H produced binds to the promoter region of the beta-globin gene of the beta-globin producing cell at −148 to −153 bp from the transcription start site of the promoter region and represses production of beta-globin proteins in the cell.

* * * * *

UNITED STATES PATENT AND TRADEMARK OFFICE
CERTIFICATE OF CORRECTION

PATENT NO. : 7,517,669 B2  Page 1 of 1
APPLICATION NO. : 10/003669
DATED : April 14, 2009
INVENTOR(S) : Robert H. Broyles and Robert A. Floyd It is certified that error appears in the above-identified patent and that said Letters Patent is hereby corrected as shown below:

In the Specification:
Column 4, line 23: After "onic" delete "a" and replace with -- α --.

Column 7, line 26: After "human" delete "a" and replace with -- α --.

Column 15, line 56: Delete "M1740" and replace with -- M61740 --.

Column 30, line 29: Delete "Cheepsunthom" and replace with -- Cheepsunthorn --.

Signed and Sealed this

Ninth Day of June, 2009

JOHN DOLL
*Acting Director of the United States Patent and Trademark Office*

SEQUENCE LISTING

<160> NUMBER OF SEQ ID NOS: 19

<210> SEQ ID NO 1
<211> LENGTH: 6
<212> TYPE: DNA
<213> ORGANISM: Homo sapiens

<400> SEQUENCE: 1 cagtgc                                                              6

```
<210> SEQ ID NO 2
<211> LENGTH: 10
<212> TYPE: DNA
<213> ORGANISM: Homo sapiens
<220> FEATURE:
<221> NAME/KEY: modified_base
<222> LOCATION: (6)..(8)
<223> OTHER INFORMATION: n = a, c, g and/or t/u

<400> SEQUENCE: 2 rtgacnnngc                                                          10

<210> SEQ ID NO 3
<211> LENGTH: 37
<212> TYPE: DNA
<213> ORGANISM: Homo sapiens

<400> SEQUENCE: 3
aactcctaag ccagtgccac aagagccaag gacaggt                            37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
aaggggggag ccagtgccag aagagccaag gacaggt                            37

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
aactcctaag ccagtgccag aaaaaacaag gacaggt                            37

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
aactcctaag ccagtgccag aacagccaac cccccgt                            37

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
aactcctaag caaaaaacag aagagccaag gacaggt                            37

<210> SEQ ID NO 8
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tcctaagcca gtgccagaag                                                 20

<210> SEQ ID NO 9
<211> LENGTH: 20
<212> TYPE: DNA
<213> ORGANISM: Gorilla gorilla

<400> SEQUENCE: 9
tcctaagcca gtgccaggag                                                 20

<210> SEQ ID NO 10
<211> LENGTH: 20
<212> TYPE: DNA
<213> ORGANISM: Macaca

<400> SEQUENCE: 10
tcctaagcca gtgccagaag                                                 20

<210> SEQ ID NO 11
<211> LENGTH: 20
<212> TYPE: DNA
<213> ORGANISM: Bos taurus

<400> SEQUENCE: 11
tctaaagtca gtgccaggaa                                                 20

<210> SEQ ID NO 12
<211> LENGTH: 20
<212> TYPE: DNA
<213> ORGANISM: Goat

<400> SEQUENCE: 12
tctaaagtca gtgccaggaa                                                 20

<210> SEQ ID NO 13
<211> LENGTH: 20
<212> TYPE: DNA
<213> ORGANISM: Ovis sp.

<400> SEQUENCE: 13
tctaaagtca gtgccaggaa                                                 20

<210> SEQ ID NO 14
<211> LENGTH: 20
<212> TYPE: DNA
<213> ORGANISM: Galago sp.

<400> SEQUENCE: 14
tcctaagtga gtgccagaac                                                 20

<210> SEQ ID NO 15
<211> LENGTH: 20
<212> TYPE: DNA
<213> ORGANISM: Tarsus

<400> SEQUENCE: 15
ctctaagcca gtaccagaac                                                 20
```

```
<210> SEQ ID NO 16
<211> LENGTH: 20
<212> TYPE: DNA
<213> ORGANISM: Lepus

<400> SEQUENCE: 16
tcctaagcca ttgccagaac                                                    20

<210> SEQ ID NO 17
<211> LENGTH: 20
<212> TYPE: DNA
<213> ORGANISM: CUNICULUS

<400> SEQUENCE: 17
tcctaagcca ttgccataac                                                    20

<210> SEQ ID NO 18
<211> LENGTH: 20
<212> TYPE: DNA
<213> ORGANISM: Rattus norvegicus

<400> SEQUENCE: 18
cctgaggcca gtggcccagc                                                    20

<210> SEQ ID NO 19
<211> LENGTH: 20
<212> TYPE: DNA
<213> ORGANISM: Mus musculus

<400> SEQUENCE: 19
tcttaagcct gtgccatagc                                                    20
```